United States Patent
Gracia Ferrer et al.

(10) Patent No.: US 7,034,016 B2
(45) Date of Patent: Apr. 25, 2006

(54) 8-PHENYL-6,9-DIHYDRO-[1,2,4]TRIAZOLO[3,4-I]PURIN-5-ONE DERIVATIVES

(75) Inventors: Jordi Gracia Ferrer, Barcelona (ES); Joan Feixas Gras, Barcelona (ES); José Manuel Prieto Soto, Barcelona (ES); Armando Vega Noverola, Barcelona (ES); Bernat Vidal Juan, Barcelona (ES)

(73) Assignee: Almirall Prodesfarma, S.A., Barcelona (ES)

( * ) Notice: Subject to any disclaimer, the term of this patent is extended or adjusted under 35 U.S.C. 154(b) by 412 days.

(21) Appl. No.: 10/057,847

(22) Filed: Jan. 25, 2002

(65) Prior Publication Data
US 2003/0060627 A1    Mar. 27, 2003

Related U.S. Application Data

(63) Continuation of application No. PCT/EP00/07062, filed on Jul. 24, 2000.

(30) Foreign Application Priority Data
Jul. 27, 1999    (ES) .................................... 9901694

(51) Int. Cl.
  *C07D 487/14*   (2006.01)
  *C07D 473/18*   (2006.01)
  *A61K 31/519*   (2006.01)
  *A61P 11/06*    (2006.01)
  *A61P 27/06*    (2006.01)

(52) U.S. Cl. ...................... 514/218; 544/115; 544/251; 540/575; 514/233.2; 514/267

(58) Field of Classification Search ................ 544/115, 544/251; 514/218, 233.2, 267, 540, 575
See application file for complete search history.

(56) References Cited

U.S. PATENT DOCUMENTS

| | | |
|---|---|---|
| 4,722,929 A | 2/1988 | Austel et al. |
| 5,990,118 A * | 11/1999 | Nagamatsu et al. ... 514/263.37 |
| 2004/0019034 A1* | 1/2004 | Vidal Juan et al. ..... 514/210.21 |

FOREIGN PATENT DOCUMENTS

| | | |
|---|---|---|
| EP | 0 149 200 A1 | 7/1985 |
| EP | 0 417 790 A2 | 3/1991 |
| EP | 0 417 790 A3 | 3/1991 |
| EP | 0 417 790 B1 | 3/1991 |
| EP | 0 463 756 A1 | 1/1992 |
| EP | 0 463 756 B1 | 1/1992 |
| GB | 2 135 311 A | 8/1984 |
| WO | WO 98/49166 A1 | 11/1998 |
| WO | WO 99/62905 A1 | 12/1999 |

OTHER PUBLICATIONS

Hamilton, H.W. et al. (1985). "Synthesis of xanthines as adenosine antagonists, a practical quantitative structure-activity relationship application," *J. Med. Chem.* 28(8): 1071-1079.

Gristwood, R.W. et al. (1992). "Studies on the cardiac actions of flosequinan in vitro," *Br. J. Pharmacol.* 105(4): 985-991.

Partial Abstract of 463756.

* cited by examiner

*Primary Examiner*—Mark L. Berch
(74) *Attorney, Agent, or Firm*—Morrison & Foerster LLP

(57) ABSTRACT

8-phenyl-6,9-dihydro-[1,2,4]triazolo[3,4-i]purin-5-one derivatives of formula (I):

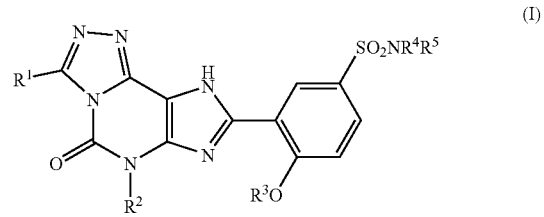

or a pharmaceutically acceptable salt thereof processes for their preparation, pharmaceutical compositions containing them and their use as PDE 5 inhibitors.

15 Claims, No Drawings

8-PHENYL-6,9-DIHYDRO-[1,2,4]TRIAZOLO [3,4-I]PURIN-5-ONE DERIVATIVES

CROSS REFERENCE TO RELATED APPLICATIONS

This application is a continuation of International Application No. PCT/EP00/07062, filed Jul. 24, 2000, and published in English on Feb. 1, 2001, which claims the benefit of Spain Application No. 9901694, filed Jul. 27, 1999, the contents of each are incorporated herein by reference.

The invention relates to new therapeutically useful 8-phenyl-6,9-dihydro-[1,2,4]triazolo[3,4-i]purin-5-one derivatives, to processes for their preparation and to pharmaceutical compositions containing them.

EP 0 417 790 relates to s-triazolo[3,4-i]purines of general formula:

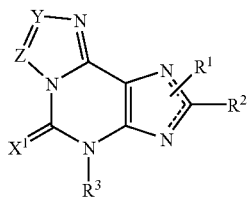

wherein Y=Z represents

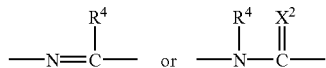

where $R^4$ represents hydrogen, alkyl, an aromatic heterocyclic group which is optionally substituted with 1 or 2 substituents independently selected from $C_1$–$C_6$ alkyl, $C_1$–$C_6$ alkoxy and halogen, or substituted or unsubstituted aryl; and $X^2$ represents oxygen, sulfur or NH;

each of $R^1$ and $R^2$ independently represents hydrogen, alkyl, cycloalkyl, aralkyl or substituted or unsubstituted aryl;

$R^3$ represents alkyl, cycloalkyl, aralkyl or substituted or unsubstituted aryl;

$X^1$ represents oxygen or sulfur;

---represents a single bond or a double bond and substituted or unsubstituted aryl means aryl which is optionally substituted with 1 or 2 substituents independently selected from $C_1$–$C_6$ alkyl, trifluoromethyl, hydroxyl, $C_1$–$C_6$ alkoxyl, $C_1$–$C_6$ alkylthio, nitro, halogen, amino, $C_1$–$C_6$ alkylamino, $C_1$–$C_6$ alkanoylamino, aroylamine, carboxyl, $C_1$–$C_6$ alkoxycarbonyl, $C_1$–$C_6$ alkanoyl and aroyl; which possess a broncho-dilatory activity, diuretic activity, renal protecting activity and/or antiamnesic activity.

We have now found that certain 8-(disubstituted)phenyl-6,9-dihydro-[1,2,4]triazolo[3,4-i]purin-5-one derivatives are potent and selective inhibitors of cyclic guanosine 3'-5'-monophosphate specific phosphodiesterase (cGMP specific PDE) and more particularly inhibitors of phosphodiesterase 5 (PDE 5), and have utility in the treatment of angina, hypertension, congestive heart failure, stroke, asthma, male erectile dysfunction, female sexual dysfunction, glaucoma and irritable bowel syndrome.

Accordingly, the present invention provides compounds which are 8-phenyl-6,9-dihydro-[1,2,4]triazolo[3,4-i]purin-5-one derivatives of formula (I):

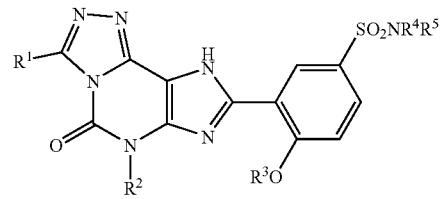

wherein:

$R^1$, $R^2$ and $R^3$ each independently represent: hydrogen; an alkyl group which is unsubstituted or substituted by a hydroxy, alkoxy, alkylthio, amino, mono- or di-alkylamino, hydroxycarbonyl, alkoxycarbonyl, acylamino, carbamoyl or alkylcarbamoyl group; or a group of formula —(CH$_2$)$_n$—R$^6$ wherein n is an integer from 0 to 4 and $R^6$ represents: a cycloalkyl group; a phenyl group which may be unsubstituted or substituted by one or more halogen atoms or alkyl, hydroxy, alkylenedioxy, alkoxy, amino, mono- or di-alkylamino, nitro, cyano or trifluoromethyl groups; or a 3 to 7-membered ring comprising from 1 to 4 heteroatoms selected from nitrogen, oxygen and sulphur, which ring may be unsubstituted or substituted by one or more halogen atoms or hydroxy, phenyl, alkoxycarbonyl, amino, mono-alkylamino, di-alkylamino or hydroxycarbonyl groups or one or more alkyl groups which may in turn be unsubstituted or substituted by one or more halogen atoms or hydroxy, alkoxy, hydroxyalkoxy, phenyl, alkoxycarbonyl, amino, mono- or di-alkylamino or hydroxycarbonyl groups;

either $R^4$ and $R^5$ together with the nitrogen atom to which they are attached form a 3 to 7-membered ring comprising a total of from 1 to 4 heteroatoms selected from nitrogen, oxygen and sulphur, which ring may be unsubstituted or substituted by one or more halogen atoms or hydroxy, oxoalkyl, carbamoyl, hydroxycarbonyl, alkoxycarbonyl, trifluoroacetyl, amino, mono- or di-alkylamino groups or an alkylene group, or one or more alkyl, alkenyl or alkynyl groups which may in turn be unsubstituted or substituted by one or more halogen atoms or hydroxy, alkoxy, hydroxyalkoxy, amino or mono- or di-alkylamino groups, or $R^4$ and $R^5$ independently represent hydrogen, an amidino group or an alkyl, alkenyl or alkynyl group which may be unsubstituted or substituted by one or more halogen atoms or hydroxy, alkoxy, alkylthio, amino, mono- or di-alkylamino groups, or $R^4$ represents hydrogen or an alkyl group and $R^5$ represents a group of formula —(CH$_2$)$_n$—R$^7$ wherein n is an integer from 0 to 4 and $R^7$ represents: a cycloalkyl group which may be unsubstituted or substituted by one or more halogen atoms or alkyl, hydroxy, alkylenedioxy, alkoxy, amino, mono- or di-alkylamino, alkylamido, nitro, cyano or trifluoromethyl groups; a phenyl group which may be unsubstituted or substituted by one or more halogen atoms or alkyl, hydroxy, alkylenedioxy, alkoxy, amino, mono- or di-alkylamino, nitro, cyano or trifluoromethyl groups; or a 3 to 7-membered ring comprising from 1 to 4 heteroatoms selected from nitrogen, oxygen and sulphur, which ring may be unsubstituted or substituted by one or more halogen atoms or hydroxy, alkoxy, phenyl, alkoxycarbonyl, amino, mono-alkylamino, di- alkylamino or hydroxycarbonyl groups or one or more alkyl groups which may be unsubstituted or substituted by one or more halogen atoms or hydroxy, alkoxy, hydroxyalkoxy, phenyl, alkoxycarbonyl, amino, mono- or di-alkylamino or hydroxycarbonyl groups;

and pharmaceutically acceptable salts thereof.

The alkyl groups and moieties such as those present in the alkoxy, hydroxyalkoxy, alkylcarbamoyl, mono- or di-alkylamino, alkylthio, alkylenedioxy, alkylamido and alkoxycarbonyl groups mentioned in relation to the groups $R^1$ to $R^7$ are usually "lower" alkyl that is containing from 1 to 6, particularly from 1 to 4 carbon atoms, the hydrocarbon chain being branched or straight. Preferred alkyl groups, and where relevant alkyl moieties, include methyl, ethyl, propyl, especially n-propyl, and butyl, especially n-butyl. Alkenyl and alkynyl groups mentioned in relation to formula (I) preferably have from 2 to 6 carbon atoms, most preferably from 2 to 4 carbon atoms.

Where an alkyl, alkenyl or alkynyl group, ring structure or moiety is described as being substituted by one or more substituents this preferably means from 1 to 3 substituents, more preferably one or two substituents.

The cycloalkyl groups mentioned in relation to the groups $R^6$ and $R^7$ are preferably $C_{3-10}$ cycloalkyl groups, more preferably $C_{3-7}$ cycloalkyl groups such as cyclopropyl, cyclobutyl, cyclopentyl, cyclohexyl and cycloheptyl groups. In compounds of the invention wherein the cycloalkyl group is substituted, preferred substituents include acetamido and mono- and di-alkylamino, most preferably mono- or di-ethylamino groups. The substituent group may be at any substitutable position of the cycloalkyl ring. Preferably the cycloalkyl ring is substituted at the 1-position.

The halogen atoms mentioned in relation to the groups $R^4$ to $R^7$ are preferably chlorine or fluorine atoms.

For compounds of the invention wherein $R^1$, $R^2$ or $R^3$ represent a group of formula

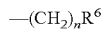
—(CH$_2$)$_n$R$^6$ n may represent 0, 1, 2, 3, or 4, preferably 0, 1 or 2.

For compounds of the invention wherein $R^6$ represents a 3 to 7-membered heterocyclic ring, $R^6$ may be unsaturated or saturated and may represent for example a piperidyl, pyrrolidyl, azetidinyl, aziridyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, triazolyl, tetrazolyl or thienyl group, which group may be substituted or unsubstituted as defined above. In preferred compounds of the invention wherein $R^1$, $R^2$ or $R^3$ represent a group of formula

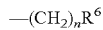
—(CH$_2$)$_n$R$^6$ and wherein $R^6$ represents a 3 to 7-membered heterocyclic ring, $R^6$ is a pyridyl, piperidyl, piperazinyl, morpholinyl, triazolyl or tetrazolyl group.

In preferred compounds of the invention $R^1$ represents: hydrogen; a $C_1$–$C_4$ alkyl group; or a group of formula

—(CH$_2$)$_n$R$^6$ wherein n is 0, 1 or 2 and $R^6$ represents phenyl, pyridyl or morpholinyl. Most preferably, $R^1$ represents hydrogen or a methyl, ethyl, propyl, pyridyl, pyridylmethyl, benzyl or N-morpholinylmethyl group.

In preferred compounds of the invention $R^2$ represents: a $C_1$–$C_5$ alkyl group especially a $C_1$–$C_4$ alkyl group; a substituted $C_1$–$C_5$ alkyl group; a $C_{3-10}$ cycloalkyl group; or a group of formula

—(CH$_2$)$_n$R$^6$ wherein n is 0, 1 or 2 and $R^6$ represents an unsubstituted or substituted phenyl or pyridyl group. Most preferably $R^2$ represents an ethyl, propyl, n-butyl, i-butyl, n-pentyl, methoxyethyl, substituted or unsubstituted benzyl or 3-pyridylmethyl group.

In preferred compounds of the invention $R^3$ represents: a $C_1$–$C_4$ alkyl group; a $C_{3-10}$ cycloalkyl group; or a group of formula

—(CH$_2$)$_n$R$^6$ wherein n is 0, 1 or 2 and $R^6$ represents an unsubstituted or substituted phenyl or pyridyl group. Most preferably $R^3$ represents an ethyl, propyl or n-butyl group.

For compounds of the invention wherein $R^4$ and $R^5$ together with the nitrogen atom to which they are attached form a 3 to 7-membered ring comprising a total of from 1 to 4 heteroatoms, the ring may be saturated or unsaturated and is preferably selected from a piperidyl, pyrrolidyl, azetidinyl, aziridyl, piperazinyl, [1,4]diazepan-1-yl, morpholinyl, thiomorpholinyl, pyrrolyl, pyrazolyl, imidazolyl, imidazolidinyl, pyrazolinyl, indolinyl or isoindolinyl group, said group being unsubstituted or substituted as defined above. It is to be understood that when the substituent is an alkylene group it is attached to the heterocyclic ring at any two substitutable positions which may be adjacent or not adjacent to each other. When the substitutable positions are not adjacent to each other, the alkylene group forms a bridging group. The alkylene group preferably has from 1 to 5 carbon atoms.

In preferred compounds of the invention the ring formed by $R^4$, $R^5$ and the nitrogen atom to which they are attached is a substituted or unsubstituted piperidyl, piperazinyl, [1,4] diazepan-1-yl, morpholinyl, pyrazolyl, azetidinyl, diazabicyclo[2.2.1]hept-2-yl or hexahydropyrrolo[2,1-a]pyrazinyl group. Preferred substituent groups are $C_1$–$C_4$ alkyl, $C_2$–$C_4$ alkenyl, carbamoyl, amino, di-$C_1$–$C_4$-alkylamino, (2-hydroxyethyl)methylamino, hydroxyl, 2,2,2-trifluoroethanoyl, 2,2,2-trifluoroethyl, formyl groups and hydroxyalkyl groups, alkoxyalkyl groups and hydroxyalkoxyalkyl groups wherein the alkyl moieties contain from 1 to 4 carbon atoms. Most preferably $R^4$ and $R^5$ together with the nitrogen atom to which they are attached represent a 4-hydroxypiperidyl, 4-carbamoylpiperidyl, 3-carbamoylpiperidyl, piperazinyl, 4-methylpiperazinyl, 4-ethylpiperazinyl, 4-formylpiperazinyl, [1,4]-diazepan-1-yl, 4-methyl-[1,4]-diazepan-1-yl, 4-(2-hydroxyethyl)piperazinyl, 4-[2-(2-hydroxyethoxy) ethyl]piperazinyl, morpholinyl, aminopyrazolyl, diazabicyclo[2.2.1]hept-2-yl, 5-methyldiazabicyclo[2.2.1]hept-2-yl, 5-(2-hydroxyethyl)-diazabicyclo[2.2.1]hept-2-yl, 3(S)-methylpiperazinyl, 3(R)-methylpiperazinyl, (3R,5S)-3,5-dimethylpiperazinyl, (2R,5S)-2,5-dimethylpiperazinyl, (2S,5R)-2,5-dimethyl piperazinyl, 3-dimethylaminoazetidinyl, 3-dimethylaminomethylazetidinyl, 4-allylpiperazinyl, 4-propylpiperazinyl, hexahydropyrrolo[1,2-a]pyrazin-2-yl, (3R,5S)-3,4,5-trimethylpiperazinyl, 4-(2-methoxyethyl)piperazinyl, 4-(2-hydroxyethyl)[1,4]diazepan-1-yl, 4-(2-hydroxy-1-methylethyl)piperazinyl, 4-(2-hydroxy-1,1-dimethylethyl)piperazinyl, 4-(2,2,2-trifluoroethyl)piperazinyl, 4-(3-hydroxypropyl)piperazinyl, 4-(isopropyl) piperazinyl, 4-(2-ethoxyethyl)piperazinyl, 4-(2,2,2-trifluoroethanoyl) piperazinyl, 3-hydroxyazetidinyl, 3-(2-hydroxyethyl)methylaminoazetidinyl or 4-(2-hydroxyethyl)-piperidyl group.

For compounds of the invention wherein $R^4$ and $R^5$ independently represent hydrogen, an amidino group or an alkyl, alkenyl or alkynyl group which may be unsubstituted or substituted by one or more hydroxy, alkoxy, alkylthio, amino, mono- or di-alkylamino groups, $R^4$ and $R^5$ are preferably hydrogen or a $C_1$–$C_4$ alkyl group which is unsubstituted or substituted by a hydroxy or dimethyl amino group, propylynyl group or an amidino group, most preferably $R^4$ and $R^5$ independently represent hydrogen or a methyl, ethyl, propyl, hydroxyethyl, dimethylaminoethyl, propynyl, dimethylaminopropyl or amidino group.

For compounds of the invention wherein $R^4$ is hydrogen or alkyl and $R^5$ represents a group of formula

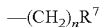
—$(CH_2)_nR^7$ n may represent 0, 1, 2, 3, or 4, preferably 0, 1, 2 or 3.

For compounds of the invention wherein $R^7$ represents a 3 to 7-membered heterocyclic ring, $R^7$ may be unsaturated or saturated and may represent for example a piperidyl, pyrrolidyl, azetidinyl, aziridyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, triazolyl, tetrazolyl or thienyl group, which group may be substituted or unsubstituted. $R^7$ may alternatively represent an unsubstituted or substituted cycloalkyl or phenyl group as defined above.

In preferred compounds of the invention $R^4$ is hydrogen or a $C_1$–$C_4$ alkyl group and $R^5$ represents a group of formula

—$(CH_2)_nR^7$ n is 0, 1, 2 or 3 and $R^7$ is a pyridyl, piperidyl, piperazinyl, morpholinyl, triazolyl, tetrazolyl, pyrrolidinyl, 1-ethylaminocyclohex-1-yl, 1-diethylaminocyclohex-1-yl, 1-ethylaminocyclohept-1-yl, 1-diethylaminocyclohept-1-yl, 3,4-dimethoxyphenyl, 1-methyl-4-phenylpiperidin-4-yl, imidazoyl, 1-methylpiperid-4-yl, tetrahydrofuranyl, 2,2,6,6,-tetramethylpiperid-4-yl, 4-hydroxypiperid-4-yl, 1-acetamidocyclohept-1-yl, 1-methyl-3-azetidinyl or 4-methylpiperazin-1-yl group. Most preferred are the compounds wherein $R^4$ represents hydrogen or a methyl or ethyl group and $R^5$ represents a pyridyl, 1-morphylinylethyl, 1-piperidylethyl, 1-morpholinylpropyl, 1-pyrrolidylethyl, 1-ethylaminocyclohexylmethyl, 1-ethylaminocycloheptylmethyl, 1-diethylaminocyclohexylmethyl, 1-diethylaminocycloheptylmethyl, 2-(3,4-dimethoxyphenyl)ethyl, 1-methyl-4-phenylpiperidin-4-ylmethyl, 1H-[1,2,4]triazol-3-yl, pyridin-4-ylmethyl,2-pyridin-2-ylethyl, 3-imidazol-1-ylpropyl, 1-methylpiperidin-4-yl, tetrahydrofuran-2-ylmethyl, 2,2,6,6-tetramethylpiperidin-4-ylmethyl, 1-acetamidocyclohept-1-ylmethyl, 1-methylazetidin-3-yl or 4-methylpiperazin-1-yl group.

Of outstanding interest are:
6-ethyl-8-[5-(4-methylpiperazine-1-sulphonyl)-2-propoxyphenyl]-6,9-dihydro-[1,2,4]triazolo[3,4-i]purin-5-one,
8-[2-butoxy-5-(4-methylpiperazine-1-sulfonyl)phenyl]-6-ethyl-6,9-dihydro-[1,2,4]triazolo[3,4-i]purin-5-one,
8-[5-(4-methylpiperazine-1-sulfonyl)-2-propoxyphenyl]-6-propyl-6,9-dihydro-[1,2,4]triazolo[3,4-i]purin-5-one,
8-{5-[4-(2-hydroxyethyl)piperazine-1-sulphonyl]-2-propoxyphenyl}-6-propyl-6,9-dihydro-[1,2,4]triazolo[3,4-i]purin-5-one,
8-[5-(4-methyl-[1,4]diazepane-1-sulfonyl)-2-propoxyphenyl]-6-propyl-6,9-dihydro-[1,2,4]triazolo[3,4-i]purin-5-one,
6-butyl-8-{5-[4-(2-hydroxyethyl)piperazine-1-sulfonyl]-2-propoxyphenyl}-6,9-dihydro-[1,2,4]triazolo[3,4-i]purin-5-one, and
3-(5-oxo-6-propyl-6,9-dihydro-5H-[1,2,4]triazolo[3,4-i]purin-8-yl)-4-propoxy-N-pyridin-4-ylbenzenesulphonamide.
8-[5-((S)-3-Methylpiperazine-1-sulfonyl)-2-propoxyphenyl]-6-propyl-6,9-dihydro-[1,2,4]triazolo[3,4-i]purin-5-one,
8-[5-((1S,4S)-5-Methyl-2,5-diazabicyclo[2.2.1]heptane-2-sulfonyl)-2-propoxyphenyl]-6-propyl-6,9-dihydro-[1,2,4]triazolo[3,4-i]purin-5-one,
8-[5-(3-Dimethylaminomethylazetidine-1-sulfonyl)-2-propoxyphenyl]-6-propyl-6,9-dihydro-[1,2,4]triazolo [3,4-i]purin-5-one,
8-[5-((3R,5S)-3,5-Dimethylpiperazine-1-sulfonyl)-2-propoxyphenyl]-6-propyl-6,9-dihydro-[1,2,4]triazolo[3,4-i]purin-5-one,
N-(3-Dimethylamino-2,2-dimethylpropyl)-3-(oxopropyl-6,9-dihydro-5H-[1,2,4]triazolo[3,4-i]purin-8-yl)-4-propoxy benzenesulfonamide,
8-{5-[4-(2-Hydroxyethyl)-[1,4]diazepane-1-sulfonyl]-2-propoxyphenyl}-6-propyl-6,9-dihydro-[1,2,4]triazolo [3,4-i]purin-5-one,
8-{5-[4-(2-Hydroxy-1,1-dimethylethyl)piperazine-1-sulfonyl]-2-propoxyphenyl}-6-propyl-6,9-dihydro-[1,2,4] triazolo[3,4-i]purin-5-one,
6-Butyl-8-{5-[4-(2-hydroxy-1,1-dimethylethyl)piperazine-1-sulfonyl]-2-propoxyphenyl}-6,9-dihydro-[1,2, 4]triazolo [3,4-i] purin-5-one According to a further feature of the present invention, the 8-phenyl-6,9-dihydro-[1,2,4]triazolo[3,4-i]purin-5-ones of general formula (I) are prepared by reaction of a corresponding hydrazinopurine derivative of formula (II):

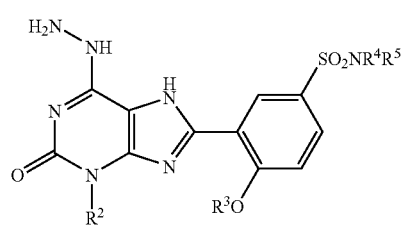

(II)

(wherein $R^2$, $R^3$, $R^4$ and $R^5$ are as hereinbefore defined) with the corresponding carboxylic acid of the general formula (III):

$R^1$—$CO_2H$ (III)

(wherein $R^1$ is as hereinbefore defined) or a reactive derivative thereof. Preferred examples of a reactive derivative of the carboxylic acid (III) are the acid halide, orthoester or anhydride. The reaction may be carried out in a solvent, preferably a polar aprotic solvent, such as N,N-dimethylformamide, dioxane, acetone or tetrahydrofuran, in the presence of an organic base, preferably an amine base, such as triethylamine and at a temperature from 15° C. to the boiling point of the solvent. The reaction can also be carried out in the absence of a solvent, in which case an excess of the carboxylic acid (III) or reactive derivative of the carboxylic acid (III) is used and the mixture is heated at a temperature from 40° C. to its boiling point. The thus obtained 8-phenyl-6,9-dihydro-[1,2,4]triazolo[3,4-i]purin-5-one derivative is then isolated by usual methods known in the art.

The hydrazinopurines of general formula (II) are obtained by reaction of the 6-thioxopurines of the general formula (IV)

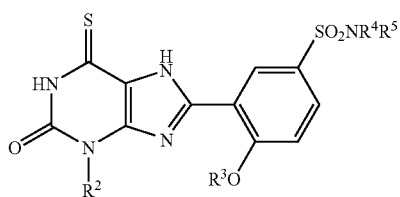

(IV)

(wherein $R^2$, $R^3$, $R^4$ and $R^5$ are as hereinbefore defined) with hydrazine hydrate at a temperature from 80 to 150° C.

The 6-thioxopurines of general formula (IV) are obtained by reaction of the 8-phenylxanthines of general formula (V)

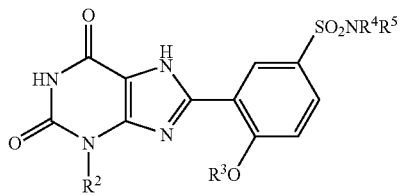

(V)

(wherein $R^2$, $R^3$, $R^4$ and $R^5$ are as hereinbefore defined) with phosphorus pentasulphide or Lawesson's reagent (2,4-bis (4-methoxyphenyl)-1,3-dithia-2,4-diphosphetane-2,4-disulphide). The reaction is preferably carried out in a solvent, such as benzene, toluene, dioxane or pyridine, at a temperature from 40° C. to the boiling point of the solvent.

The 8-phenylxanthines of general formula (V) are prepared from the corresponding compound of formula (VI):

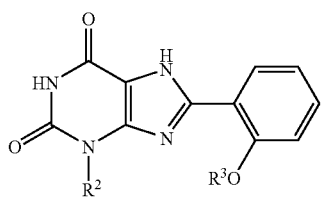

(VI)

(wherein $R^2$ and $R^3$ are as defined above) by reaction with chlorosulphonic acid (preferably in excess), preferably under a nitrogen atmosphere and at a temperature from −5 ° C. to 10 ° C. and where the solvent is the same chlorosulphonic acid. In this manner, the sulphonyl chloride of formula (VII):

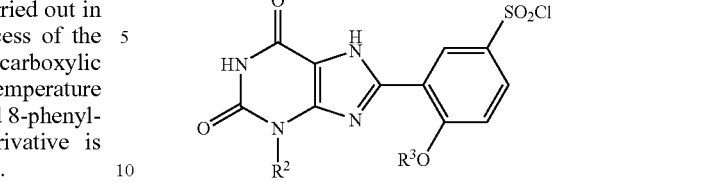

(VII)

wherein $R^2$ and $R^3$ are as defined above, is obtained, which by further reaction with the corresponding amine (VIII):

$$HN\begin{matrix}R^4\\R^5\end{matrix}$$ (VIII)

wherein $R^4$ and $R^5$ are as defined above, produces the 8-phenylxanthine derivative of general formula (VI). The reaction is carried out in an organic solvent preferably a polar aprotic organic solvent such as dioxane, methylene chloride or tetrahydrofuran, at a temperature from 10° C. to the boiling point of the solvent and in the presence of an organic base, preferably an amine base such as triethylamine.

The 8-phenyl-6,9-dihydro-[1,2,4]triazolo[3,4-i]purin-5-ones derivatives of general formula (I) are also prepared according to a further feature of the present invention, from the corresponding phenylxanthine of formula (IX):

(IX)

(wherein $R^1$, $R^2$ and $R^3$ are as hereinbefore defined) by reaction with chlorosulphonic acid (preferably in excess), preferably under a nitrogen atmosphere and at a temperature from −5° C. to 10° C. and where the solvent is the same chlorosulphonic acid. In this manner, the sulphonyl chloride of formula (X):

(X)

wherein $R^1$, $R^2$ and $R^3$ are as defined above, is obtained, which by further reaction with the corresponding amine (VIII):

(VIII)

wherein R⁴ and R⁵ are as defined above, gives the 8-phenyl-6,9-dihydro-[1,2,4]triazolo[3,4-i]purin-5-one derivative of general formula (I). The reaction is carried out in an organic solvent preferably a polar aprotic organic solvent such as dioxane, methylene chloride or tetrahydrofuran, at a temperature from 10° C. to 40° C. and in the presence of an organic base, preferably an amine base such as triethylamine. The thus obtained 8-phenyl-6,9-dihydro-[1,2,4]triazolo[3,4-i]purin-5-one derivative is then isolated by the usual method known in the art.

The intermediate compounds of formula (IX) can be prepared by reaction of a corresponding hydrazinopurine derivative of formula (XI):

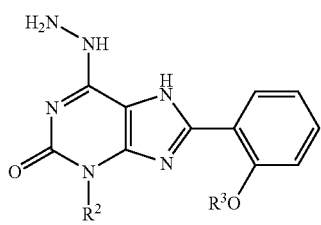
(XI)

(wherein R² and R³ are as hereinbefore defined) and the corresponding carboxylic acid of the general formula (III):

R¹—CO₂H (III)

(wherein R¹ is as hereinbefore defined) or a reactive derivative of thereof. The reactive derivative of the carboxylic acid (III) is preferably the acid halide, orthoester or anhydride. The reaction can be carried out in a solvent, preferably a polar aprotic solvent, such as N,N-dimethylformamide, dioxane, acetone or tetrahydrofuran, in the presence of an organic base, preferably an amine base, such as triethylamine and at a temperature from 15° C. to 40° C. The reaction can also be carried out in the absence of a solvent, in which case an excess of the carboxylic acid (III) or reactive derivative of the carboxylic acid (III) is used and the mixture is heated at a temperature from 40° C. to its boiling point.

The hydrazinopurines of general formula (XI) are obtained by reaction of the 6-thioxopurines of the general formula (XII)

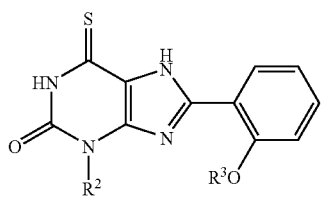
(XII)

(wherein R² and R³ are as hereinbefore defined) with hydrazine hydrate at a temperature from 80 to 150° C.

The 6-thioxopurines of general formula (XII) are obtained by reaction of the 8-phenylxanthines of general formula (VI)

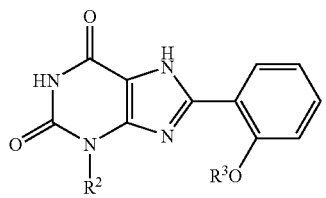
(VI)

(wherein R² and R³ are as hereinbefore defined) with phosphorus pentasulphide or Lawesson's reagent (2,4-bis(4-methoxyphenyl)-1,3-dithia-2,4-diphosphetane-2,4-disulphide). The reaction is preferably carried out in a solvent, such as benzene, toluene, dioxane or pyridine, at a temperature from 40° C. to the boiling point of the solvent.

The 8-phenylxanthines of general formula (VI) can be prepared by reaction of the corresponding 5,6-diaminouracils and the corresponding salicylic acid derivatives by methods known per se, e.g. H. W. Hamilton et al., *J. Med. Chem.* 1985, 28, 1071–1079 and references cited therein.

The 8-phenyl-6,9-dihydro-[1,2,4]triazolo[3,4-i]purin-5-one derivatives of formula (I) can be converted by methods known per se into pharmaceutically acceptable salts, preferably acid addition salts by treatment with organic or inorganic acids such as fumaric, tartaric, succinic or hydrochloric acid. Also 8-phenyl-6,9-dihydro-[1,2,4]triazolo[3,4-i]purin-5-one derivatives of formula (I) in which there is the presence of an acidic group, may be converted into pharmacologically acceptable by reaction with an alkali metal hydroxide or an organic base such as sodium or potassium hydroxide. The acid or alkali addition salts so formed may be interchanged with suitable pharmaceutically acceptable counter ions using process known per se.

The cyclic GMP specific phosphodiesterase (PDE 5) was isolated from human platelet lysates by ion exchange chromatography using a Mono-Q column. The enzyme activity was determined using 0.25 mM [3H]-cyclic GMP as substrate. The purification of the enzyme and the assessment of the PDE 5 inhibitory activity of our compounds were performed essentially as described by Gristwood et al., *Br. J. Pharmacol.* 1992, 105, 985–991.

The results are shown in Table 1.

TABLE 1

| Example | IC₅₀ (nM) |
|---------|-----------|
| 4       | 11        |
| 6       | 13        |
| 17      | 1.5       |
| 18      | 14        |
| 22      | 3.7       |
| 27      | 4         |
| 43      | 4         |
| 86      | 1.4       |
| 89      | 0.51      |
| 91      | 0.97      |
| 93      | 0.85      |
| 101     | 0.54      |
| 105     | 0.34      |
| 108     | 1.6       |
| 138     | 0.84      |

It can be seen from Table 1 that the compounds of formula (I) are potent inhibitors of cyclic GMP specific phosphodiesterase (PDE 5). Preferred 8-phenyl-6,9-dihydro-[1,2,4]triazolo[3,4-i]purin-5-one derivatives of the invention possess an $IC_{50}$ value for the inhibition of PDE 5 (determined as defined above) of less than 30 nM, preferably less than 20 nM and most preferably less than 15 nm. The 8phenyl-6,9-dihydro-[1,2,4]triazolo[3,4-i]purin-5-one derivatives of the invention are useful in a the treatment of stable, unstable and variant angina, hypertension, pulmonary hypertension, congestive heart failure, renal failure, atherosclerosis, conditions of reduced blood vessel potency, peripheral vascular disease, vascular disorders (e.g. Raynaud=s disease), stroke, bronchitis, chronic asthma, allergic asthma, allergic rhinitis, glaucoma, male erectile dysfunction, female sexual dysfunction and diseases characterised by disorders of gut motility, e.g. irritable bowel syndrome.

Accordingly, the 8-phenyl-6,9-dihydro-[1,2,4]triazolo[3,4-i]purin-5-one derivatives of the invention and pharmaceutically acceptable salts thereof, and pharmaceutical compositions comprising such compound and/or salts thereof, may be used in a method of treatment of disorders of the human body which comprises administering to a patient requiring such treatment an effective amount of a 8-phenyl-6,9-dihydro-[1,2,4]triazolo[3,4-i]purin-5-one derivative of the invention or a pharmaceutically acceptable salt thereof.

The present invention also provides pharmaceutical compositions which comprise, as an active ingredient, at least a 8-phenyl-6,9-dihydro-[1,2,4]triazolo[3,4-i]purin-5-one derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 10–600 mg of active ingredient per day. Daily dosage may be administered in one or more treatments, preferably from 1 to 4 treatments, per day.

The syntheses of the compounds of the invention and of the intermediates for use therein are illustrated by the following Examples (including Preparation Examples (Preparations 1–37)) which do not limit the scope of the invention in any way.

$^1$H Nuclear Magnetic Resonance Spectra were recorded on a Varian Gemini 300 spectrometer. Low Resolution Mass Spectra (m/z) were recorded on a Micromass ZMD mass spectrometer using ESI ionization. Melting points were recorded using a Perkin Elmer DSC-7 apparatus. The chromatographic separations were obtained using a Waters 2690 system equipped with a Symmetry C18 (2.1×10 mm, 3.5 µM) column. The mobile phase was formic acid (0.4 mL), ammonia (0.1 mL), methanol (500 mL) and acetonitrile (500 mL) (A) and formic acid (0.46 mL), ammonia (0.115 mL) and water (1000 mL) (B): initially from 0% to 95% of B in 20 min, and then 4 min. with 95% of B. The reequilibration time between two injections was 5 min. The flow rate was 0.4 mL/min. The injection volume was 5 µL. Diode array chromatograms were collected at 210 nM.

PREPARATION EXAMPLES

Preparation 1

8-(2-Ethoxyphenyl)-6-ethyl-6,9-dihydro-[1,2,4]triazolo[3,4-i]purin-5-one a) A solution of 2-ethoxybenzoyl chloride (12.0 g, 65 mmol) in dimethylformamide (10 mL) was added dropwise to a stirred solution of 5,6-diamino-1-ethyl-1H-pyrimidine-2,4-dione (10.4 g, 61 mmol) and triethylamine (9.8 mL, 65 mmol) in dimethylformamide (250 mL). The resulting mixture was stirred for 20 hours at room temperature, then evaporated under reduced pressure. Aqueous sodium hydroxide solution (1N, 98 mL, 98 mmol) was added and the mixture heated under reflux for 6 hours. The resulting solution was acidified with 1N hydrochloric acid and the precipitate collected and dried by suction to give 8-(2-ethoxyphenyl)-3-ethyl-3,7-dihydropurine-2,6-dione as a beige solid (7.0 g, 72%).

b) Phosphorus pentasulphide (5.5 g, 12.4 mmol) was added portionwise to a stirred suspension of the above compound (7.0 g, 23.3 mmol) in pyridine (115 mL) and the resulting mixture stirred under reflux for 3 hours, then evaporated under reduced pressure. The residue was triturated with hydrochloric acid (2N, 100 mL) and the precipitate collected by filtration and dried under vacuum to yield 8-(2-ethoxyphenyl)-3-ethyl-6-mercapto-3,7-dihydropurin-2-one (6.9 g, 95%) as a pale brown solid.

c) A stirred mixture of the above compound (6.9 g, 21.8 mmol) and hydrazine monohydrate (100 mL) was heated to 130 C. for 3 hours. The resulting mixture was cooled and the precipitate collected by filtration and washed with water and ethanol, then dried under vacuum to yield 8-(2-ethoxyphenyl)-3-ethyl-6-hydrazino-3,7-dihydropurin-2-one (6.6 g, 97%) as an off-white solid.

d) A stirred mixture of the above compound (6.6 g, 21.0 mmol) and formic acid (110 mL) was heated under reflux for 2 hours. The resulting solution was concentrated under vacuum and the residue partitioned between dichloromethane and aqueous sodium bicarbonate solution, then the organic phase separated, washed with water, dried (MgSO$_4$) and evaporated under reduced pressure to yield the title product (5.4 g, 79%) as an off-white solid.

δ (DMSO-d6): 1.38 (3H,t), 1.49 (3H,t), 4.27 (4H,m), 7.08 (1H,t), 7.21 (1H,d), 7.47 (1H,t), 7.97 (1H,d), 9.21 (1H,s).

Preparation 2

4-Ethoxy-3-(6-ethyl-5-oxo-6,9-dihydro-5H-[1,2,4]triazolo[3,4-i]purin-8-yl)benzenesulphonyl chloride The title compound of Preparation 1 (5.4 g, 16.6 mmol) was added portionwise to neat ice-cooled chlorosulphonic acid (16 mL) and the resulting mixture stirred at 0 C. for 30 minutes and at room temperature overnight. The reaction mixture was carefully poured into stirred ice-water and the precipitate collected by filtration and dried under reduced pressure to yield the title compound (6.4 g, 91%) as a white solid.

δ (DMSO-d6): 1.42 (6H,m), 4.33 (2H,q), 4.42 (2H,q), 7.23 (1H,d), 7.73 (1H,d), 8.39 (1H,s), 9.59 (1H,s).

Preparation 3

6-Ethyl-8-(2-propoxyphenyl)-6,9-dihydro-[1,2,4]triazolo[3,4-i]purin-5-one

Obtained as a white solid (51% overall) from 5,6-diamino-1-ethyl-1H-pyrimidine-2,4-dione and 2-propoxybenzoyl chloride by the procedure described in Preparation 1.

δ (DMSO-d6): 1.15 (t, 3 H), 1.51 (t, 3 H), 2.05 (m, 2 H), 4.22 (t, 2 H), 4.44 (q, 2 H), 7.05 (d, 1 H), 7.12 (t, 1 H), 7.42 (t, 1 H), 8.40 (d, 1 H), 8.95 (s, 1 H), 11.40 (bs, 1 H).

Preparation 4

3-(6-Ethyl-5-oxo-6,9-dihydro-5H-[1,2,4]triazolo[3,4-i]purin-8-yl)-4-propoxybenzenesulphonyl chloride Obtained as a white solid (74%) from the title compound of Preparation 3, using the procedure described in Preparation 2.

δ (DMSO-d6): 0.95 (t, 3 H), 1.39 (t, 3 H), 1.82 (m, 2 H), 4.33 (m, 4 H), 7.22 (d, 1 H), 7.75 (d, 1 H), 8.28 (s, 1 H), 9.55 (s, 1 H), 14.4 (bs, 1 H).

Preparation 5

8-(2-Butoxyphenyl)-6-ethyl-6,9-dihydro-[1,2,4]triazolo[3,4-i]purin-5-one

Obtained as a white solid (70% overall) from 5,6-diamino-1-ethyl-1H-pyrimidine-2,4-dione and 2-butoxybenzoyl chloride by the procedure described in Preparation 1.

δ (DMSO-d6): 1.05 (t, 3 H), 1.51 (m, 5 H), 1.95 (m, 2 H), 4.25 (t, 2 H), 4.45 (q, 2 H), 7.05 (d, 1 H), 7.13 (t, 1 H), 7.42 (t, 1 H), 8.40 (d, 1 H), 8.95 (s, 1 H), 11.55 (bs, 1 H).

Preparation 6

4-Butoxy-3-(6-ethyl-5-oxo-6,9-dihydro-5H-[1,2,4]triazolo[3,4-i]purin-8-yl)benzenesulphonyl chloride Obtained as a white solid (42%) from the title compound of Preparation 5, using the procedure described in Preparation 2.

δ (DMSO-d6): 0.95 (t, 3 H), 1.40 (m, 5 H), 1.80 (m, 2 H), 4.32 (m, 4 H), 7.22 (d, 1 H), 7.75 (d, 1 H), 8.38 (s, 1 H), 9.55 (s, 1 H), 13.0 (bs, 1 H).

Preparation 7

8-(2-Ethoxyphenyl)-6-propyl-6,9-dihydro-[1,2,4]triazolo[3,4-i]purin-5-one

Obtained as a white solid (28% overall) from 5,6-diamino-1-propyl-1H-pyrimidine-2,4-dione and 2-ethoxybenzoyl chloride by the procedure described in Preparation 1.

δ (DMSO-d6): 0.96 (3H,t), 1.41 (3H,t), 1.83 (2H,m), 4.18 (2H,t), 4.28 (2H,q), 7.09 (1H,t), 7.20 (1H,d), 7.46 (1H,t), 7.93 (1H,d), 9.21 (1H,s).

Preparation 8

4-Ethoxy-3-(5-oxo-6-propyl-6,9-dihydro-5H-[1,2,4]triazolo[3,4-i]purin-8-yl)benzenesulphonyl chloride Obtained as a white solid (73%) from the title compound of Preparation 7, using the procedure described in Preparation 2.

δ (DMSO-d6): 0.99 (3H,t), 1.42 (3H,t), 1.89 (2H,m), 4.22 (2H,t), 4.32 (2H,q), 7.19 (1H,d), 7.69 (1H,d), 8.26 (1H,s), 9.33 (1H,s).

Preparation 9

8-(2-Propoxyphenyl)-6-propyl-6,9-dihydro-[1,2,4]triazolo[3,4-i]purin-5-one

Obtained as a beige solid (21% overall) from 5,6-diamino-1-propyl-1H-pyrimidine-2,4-dione and 2-propoxybenzoyl chloride by the procedure described in Preparation 1.

δ (DMSO-d6): 0.96 (3H,t), 0.99 (3H,t), 1.83 (4H,m), 4.17 (4H,m), 7.10 (1H,t), 7.22 (1H,d), 7.49 (1H,t), 7.96 (1H,d), 9.22 (1H,s).

Preparation 10

3-(5-Oxo-6-propyl-6,9-dihydro-5H-[1,2,4]triazolo[3,4-i]purin-8-yl)-4-propoxybenzenesulphonyl chloride Obtained as a white solid (100%) from the title compound of Preparation 9, using the procedure described in Preparation 2.

δ (DMSO-d6): 0.98 (6H,m), 1.88 (4H,m), 4.26 (4H,m), 7.23 (1H,d), 7.71 (1H,d), 8.30 (1H,s), 9.50 (1H,s).

Preparation 11

6-Butyl-8-(2-ethoxyphenyl)-6,9-dihydro-[1,2,4]triazolo[3,4-i]purin-5-one

Obtained as an off-white solid (49% overall) from 5,6-diamino-1-butyl-1H-pyrimidine-2,4-dione and 2-ethoxybenzoyl chloride by the procedure described in Preparation 1.

δ (CDCl$_3$): 1.02 (3H,t), 1.48 (2H,m), 1.63 (3H,t), 1.88 (2H,m), 4.39 (4H,m), 7.07 (1H,d), 7.16 (1H,t), 7.42 (1H,d), 8.41 (1H,d), 8.93 (1H,s), 11.37 (1H,bs).

Preparation 12

3-(6-Butyl-5-oxo-6,9-dihydro-5H-[1,2,4]triazolo[3,4-i]purin-8-yl)-4-ethoxybenzenesulphonyl chloride Obtained as a white solid (90%) from the title compound of Preparation 11, using the procedure described in Preparation 2.

δ (CDCl$_3$): 0.96 (3H,t), 1.42 (5H,m), 1.82 (2H,m), 4.28 (2H,t), 4.39 (2H,q), 7.20 (1H,d), 7.72 (1H,d), 8.29 (1H,s), 9.43 (1H,s).

Preparation 13

6-Butyl-8-(2-propoxyphenyl)-6,9-dihydro-[1,2,4]triazolo[3,4-i]purin-5-one

Obtained as a beige solid (41% overall) from 5,6-diamino-1-butyl-1H-pyrimidine-2,4-dione and 2-propoxybenzoyl chloride by the procedure described in Preparation 1.

δ (CDCl$_3$): 1.03 (3H, t), 1.12 (3H, t), 1.50 (2H, m) 1.90 (2H, m), 2.05 (2H, m), 4.26 (2H, t), 4.39 (2H, t), 7.12 (2H, m), 7.43 (1H, t), 8.40 (1H, d), 8.95 (1H, s), 11.36 (1H, m).

Preparation 14

3-(6-Butyl-5-oxo-6,9-dihydro-5H-[1,2,4]triazolo[3,4-i]purin-8-yl)-4-propoxybenzenesulphonyl chloride Obtained as a white solid (86%) from the title compound of Preparation 13, using the procedure described in Preparation 2.

δ (CDCl$_3$): 1.05 (6H, m), 1.50 (2H, m), 1.95 (4H, m) 4.40 (4H, m), 7.35 (1H, d), 8.10 (1H, d), 8.82 (1H, s), 9.05 (1H, s).

Preparation 15

8-(2-Butoxyphenyl)-6-butyl-6,9-dihydro-[1,2,4]triazolo[3,4-i]purin-5-one

Obtained as a beige solid (22% overall) from 5,6-diamino-1-butyl-1H-pyrimidine-2,4-dione and 2-butoxybenzoyl chloride by the procedure described in Preparation 1.

δ (CDCl$_3$): 1.02 (6H,m), 1.55 (4H,m), 1.95 (4H,m), 4.35 (4H,m), 7.10 (2H,m), 7.42 (1H,m), 8.40 (1H,d), 8.95 (1H,s), 11.43 (1H,bs).

Preparation 16

4-Butoxy-3-(6-butyl-5-oxo-6,9-dihydro-5H-[1,2,4]triazolo[3,4-i]purin-8-yl)benzenesulphonyl chloride Obtained as a white solid (77%) from the title compound of Preparation 15, using the procedure described in Preparation 2.

δ (CDCl$_3$): 1.03 (6H, m), 1.52 (4H, m), 1.95 (4H, m) 4.41 (4H, m), 7.25 (1H, d), 8.09 (1H, d), 8.95 (1H, s), 9.03 (1H, s), 11.94 (1H, bs).

Preparation 17

3-Methyl-8-(2-propoxyphenyl)-6-propyl-6,9-dihydro-[1,2,4]triazolo[3,4-i]purin-5-one A mixture of 8-(2-propoxyphenyl)-3-propyl-6-hydrazino-3,7-dihydropurin-2-one (1.0 g, 2.9 mmol, see Preparation 9) and triethyl orthoacetate (10 mL) was heated under reflux for 2 h. The resulting mixture was cooled and the precipitate collected by filtration and washed with water and ethanol, then dried under vacuum to yield the title compound (0.82 g, 77%) as an off-white solid.

δ (DMSO-d6): 0.92 (3H, t), 0.96 (3H, t), 1.82 (4H, m), 2.77 (3H, s), 4.24 (4H, m), 7.08 (1H, t), 7.20 (1H, d), 7.45 (1H, t), 7,92 (1H, d)

Preparation 18

3-(3-Methyl-5-oxo-6-propyl-6,9-dihydro-5H-[1,2,4]triazolo[3,4-i]purin-8-yl)-4-propoxybenzenesulfonyl chloride Obtained as a white solid (88%) from the title compound of Preparation 17, using the procedure described in Preparation 2.

δ (CDCl$_3$): 1.10 (4H, m), 1.96 (2H, m), 2.09 (2H, m), 2.96 (3H, s), 4.32 (2H, t), 4.48 (2H, t), 7.28 (1H, d), 8.09 (1H,d), 9.07 (1H, s), 11.8 (1H, bs)

Preparation 19

6-Hydrazino-8-[5-(4-methylpiperazine-1-sulfonyl)-2-propoxyphenyl]-3-propyl-3,7-dihydropurin-2-one a) Phosphorus pentasulphide (0.7 g, 3.1 mmol) was added portionwise to a stirred suspension of 8-[5-(4-methylpiperazine-1-sulfonyl)-2-propoxyphenyl]-3-propyl-3,7-dihydropurine-2,6-dione (1.5 g, 23.3 mmol) in pyridine (15 mL) and the resulting mixture stirred under reflux for 3 hours, then evaporated under reduced pressure to give crude 8-(2-propoxyphenyl)-3-propyl-6-mercapto-3,7-dihydropurin-2-one (1.38 g) which was used directly in the next step.

δ (DMSO-d6): 0.89 (3H, t), 1.03 (3H, t), 1.75 (2H, m), 1.82 (2H, m), 2.15 (3H, s), 2.37 (4H, m), 2.92 (4H, m), 3.97 (2H, t), 4.20 (2H, t), 7.42 (1H, d), 7.82 (1h, d), 8.16 (1H, s), 12.34 (1H, bs), 12.67 (1H, bs).

b) A stirred mixture of the above compound (1.38 g) and hydrazine monohydrate (15 mL) was heated to 130° C. for 3 hours. The resulting mixture was cooled and the precipitate collected by filtration and washed with water and ethanol, then dried under vacuum to yield 6-hydrazino-8-[5-(4-methylpiperazine-1-sulfonyl)-2-propoxyphenyl]-3-propyl-3,7-dihydropurin-2-one (1.08 g, 70% overall) as an off-white solid.

δ (DMSO-d6): 0.89 (3H, t), 1.04 (3H, m), 1.70 (2H, m), 1.89 (2H, m), 2.13 (3H, s), 2.36 (4H, m), 2.91 (4H, m), 3.96 (2H,m), 4.28 (2H, m), 7.51 (1H, d), 7.81 (1H, d), 8.51 (1H, s).

Preparation 20

6-Hydrazino-8-[5-(piperazine-1-sulfonyl)-2-propoxyphenyl]-3-propyl-1,3,6,7-tetrahydropurin-2-one Obtained as a beige solid (10% overall) from 8-[5-(piperazine-1-sulfonyl)-2-propoxyphenyl]-3-propyl-3,7-dihydropurine-2,6-dione by the procedure described in Preparation 19.

δ (DMSO-d6): 0.89 (3H, t), 1.06 (3H, m), 1.72 (2H, m), 1.91 (2H, m), 2.71 (4H, m), 2.82 (4H, m), 3.96 (2H, m), 4.28 (2H, m), 7.51 (1H, d), 7.88 (1H, d), 8.52 (1H, s).

Preparation 21

6-Hydrazino-8-[5-(4-methyl-[1,4]diazepane-1-sulfonyl)-2-propoxyphenyl]-3-propyl-1,3,6,7-tetrahydropurin-2-one Obtained as an off-white solid (91% overall) from 8-[5-(4-methyl-[1,4]diazepane-1-sulfonyl)-2-propoxyphenyl]-3-propyl-3,7-dihydropurine-2,6-dione by the procedure described in Preparation 19.

δ (DMSO-d6): 0.89 (3H, t), 1.04 (3H, m), 1.72 (4H, m), 1.92 (2H, m), 2.22 (3H, s), 2.4–2.6 (6H, m), 3.38 (4H, m) 3.98 (2H, t), 4.28 (2H, t), 7.44 (1H, d), 7.86 (1H, d), 8.58 (1H, s).

Preparation 22

6-Hydrazino-8-[5-(morpholine-4-sulfonyl)-2-propoxyphenyl]-3-propyl-3,7-dihydropurin-2-one Obtained as a beige solid (16% overall) from 8-[5-(morpholine-4-sulfonyl)-2-propoxyphenyl]-3-propyl-3,7-dihydropurine-2,6-dione by the procedure described in Preparation 19.

δ (DMSO-d6): 0.88 (3H, t), 1.03 (3H, m), 1.75 (2H, m) 1.92 (2H, m), 2.92 (4H, m), 3.64 (4H, m), 3.96 (2H, m), 4.25 (2H, m), 7.52 (1H, m), 7.79 (1H, m), 8.51 (1H, s).

Preparation 23

8-[2-Butoxy-5-(4-methylpiperazine-1-sulfonyl)phenyl]-6-hydrazino-3-propyl-3,7-dihydropurin-2-one Obtained as a beige solid (71% overall) 8-[2-butoxy-5-(4-methylpiperazine-1-sulfonyl)phenyl]-3-propyl-3,7-dihydropurine-2,6-dione by the procedure described in Preparation 19.

δ (DMSO-d6): 0.92 (6H,m), 1.52 (2H, m), 1.89 (4H, m), 2.12 (3H, s), 2.37 (4H, m), 2.92 (4H, m), 3.99 (2H, t), 4.26 (2H, t), 7.48 (1H, d), 7.84 (1H, d), 8.17 (1H, s).

Preparation 24

8-[2-Butoxy-5-(morpholine-4-sulfonyl)phenyl]-6-hydrazino-3-propyl-3,7-dihydropurin-2-one Obtained as a beige solid (30% overall) from 8-[2-butoxy-5-(morpholine-4-sulfonyl)phenyl]-3-propyl-3,7-dihydropurine-2,6-dione by the procedure described in Preparation 19.

δ (DMSO-d6): 0.92 (6H, m), 1.46 (2H, m), 1.68 (2H, m), 1.82 (2H, m), 2.86 (4H, m), 3.60 (4H, m), 3.94 (2H, t), 4.32 (2H, m), 7.50 (1H, d), 7.80 (1H, d), 8.49 (1H, s).

Preparation 25

8-(2-Propoxyphenyl)-6-pyridin-2-ylmethyl-6,9-dihydro-[1,2,4]triazolo[3,4-i]purin-5-one Obtained as a beige solid (19% overall) from 5,6-diamino-1-pyridin-2-ylmethyl-1H-pyrimidine-2,4-dione and 2-propoxybenzoyl chloride by the procedure described in Preparation 1.

Preparation 26

3-(5-Oxo-6-pyridin-2-ylmethyl-6,9-dihydro-5H-[1,2,4]triazolo[3,4-i]purin-8-yl)-4-propoxybenzenesulfonyl chloride Obtained as a white solid (65%) from the title compound of Preparation 25, using the procedure described in Preparation 2.

Preparation 27

6-Butyl-8-(2-propoxyphenyl)-3-propyl-6,9-dihydro-[1,2,4]triazolo[3,4-i]purin-5-one Obtained as a white solid (28% overall) from 5,6-diamino-1-butyl-1H-pyrimidine-2,4-dione and 2-propoxybenzoyl chloride by the procedure described in Preparation 1, using trimethyl orthobutyrate instead of formic acid in the last step.

Preparation 28

3-(6-Butyl-5-oxo-3-propyl-6,9-dihydro-5H-[1,2,4]triazolo[3,4-i]purin-8-yl)-4-propoxybenzenesulfonyl chloride Obtained as a white solid (86%) from the title compound of Preparation 27, using the procedure described in Preparation 2.

Preparation 29

6-Isobutyl-8-(2-propoxyphenyl)-6,9-dihydro-[1,2,4]triazolo[3,4-i]purin-5-one Obtained as a white solid (21% overall) from 5,6-diamino-1-isobutyl-1H-pyrimidine-2,4-dione and 2-propoxybenzoyl chloride by the procedure described in Preparation 1.

δ (DMSO-d6): 0.93 (9H, m), 1.80 (2H, m), 2.36 (1H, m), 4.02 (2H, d), 4.12 (2H, t), 7.09 (1H, t), 7.18 (1H, d), 7.44 (1H, t), 7.92 (1H, d), 9.20 (1H, s).

Preparation 30

3-(6-Isobutyl-5-oxo-6,9-dihydro-5H-[1,2,4]triazolo[3,4-i]purin-8-yl)-4-propoxybenzenesulfonyl chloride Obtained as a white solid (62%) from the title compound of Preparation 29, using the procedure described in Preparation 2.

δ (DMSO-d6): 1.01 (9H, m), 1.86 (2H, m), 2.36 (1H, m), 4.06 (2H, d), 4.19 (2H, t), 7.18 (1H, d), 7.66 (1H, d), 8.18 (1H, s), 9.27 (1H, s).

Preparation 31

6-Pentyl-8-(2-propoxyphenyl)-6,9-dihydro-[1,2,4]triazolo[3,4-i]purin-5-one

Obtained as a white solid (19% overall) from 5,6-diamino-1-pentyl-1H-pyrimidine-2,4-dione and 2-propoxybenzoyl chloride by the procedure described in Preparation 1.

δ (DMSO-d6): 0.83 (3H, t), 0.96 (3H, t), 1.33 (4H, m), 1.82 (4H, m), 4.15 (4H, m), 7.06 (1H, t), 7.19 (1H, d), 7.42 (1H, t), 7.91 (1H, d), 9.19 (1H, s).

Preparation 32

3-(5-Oxo-6-pentyl-6,9-dihydro-5H-[1,2,4]triazolo[3,4-i]purin-8-yl)-4-propoxybenzenesulphonyl chloride Obtained as a white solid (55%) from the title compound of Preparation 31, using the procedure described in Preparation 2.

δ (DMSO-d6): 0.88 (3H, m), 0.98 (3H, t), 1.38 (4H, m), 1.82 (4H, m), 4.26 (4H, m), 7.20 (1H, d), 7.68 (1H, d), 8.22 (1H, s), 9.38 (1H, s).

Preparation 33

6-(2-Methoxyethyl)-8-(2-propoxyphenyl)-6,9-dihydro-[1,2,4]triazolo[3,4-i]purin-5-one Obtained as a white solid (65% overall) 5,6-diamino-1-(2-methoxyethyl)-1H-pyrimidine-2,4-dione and 2-propoxybenzoyl chloride by the procedure described in Preparation 1.

Preparation 34

3-[6-(2-Methoxyethyl)-5-oxo-6,9-dihydro-5H-[1,2,4]triazolo[3,4-i]purin-8-yl]-4-propoxybenzenesulfonyl chloride Obtained as a white solid (95%) from the title compound of Preparation 33, using the procedure described in Preparation 2.

Preparation 35

Azetidin-3-ylmethyldimethylamine, dihydrochloride a) A solution of 1-(1,1-diphenylmethyl)azetidine-3-carbonitrile (7.8 g, 31.4 mmol) in 30 mL of tetrahydrofuran was slowly added to a suspension of lithium aluminium hydride (4.0 g, 105 mmol) in tetrahydrofuran under nitrogen and the resulting mixture was stirred under reflux for one hour. On cooling, the mixture was treated dropwise with water (4 mL), aqueous sodium hydroxyde (4 mL, 4N), and water (12 mL) and filtered. The filtrate was concentrated under reduced pressure to yield 3-(aminomethyl)-1-(1,1-diphenylmethyl)azetidine as a white solid (5.2 g, 73%).

b) A mixture of 3-(aminomethyl)-1(1,1-diphenyl methyl) azetidine (10.9 g, 43 mmol), formaldehyde (21.8 mL) and formic acid (21.8 mL) was stirred under reflux for one hour and then evaporated under reduced pressure. The resulting residue was mixed with ice, basified with aqueous sodium hydroxyde 2N and extracted with dichloromethane. The organic solution was washed with water, brine, dried (MgSO₄) and evaporated under reduced pressure to yield [1-(1,1-diphenylmethyl)azetidin-3-ylmethyl]dimethylamine (10.4 g, 86%) as an oil.

δ (CDCl₃): 2.16 (6H, s), 2.44 (2H, d), 2.6–2.8 (4H, m), 3.38 (2H, t), 4.32 (1H, s), 7.1–7.3 (10 H, m).

c) Hydrogen chloride in methanol was added to a mixture of [1-(1,1-diphenylmethyl)azetidin-3-ylmethyl]dimethylamine (9.9 g, 35 mmol) in methanol (150 mL) until pH=4. Palladium hydroxyde (1.5 g, 20%) was added and the resulting mixture hydrogenated at room temperature at 50 p.s.i. for 4 days. The mixture was filtered through Celite and the filtrate evaporated under reduced pressure to give the title compound (5.0 g, 76%) as a white solid.

δ (DMSO-d6): 2.72 (6H, s), 3,2–4.1 (8H, m).

Preparation 36

(1S,4S)-2-(2,5-Diazabicyclo[2.2.1]hept-2-yl)ethanol, dihydrochloride a) A mixture of (1S,4S)-2,5-diazabicyclo[2–2.1]heptane-2-carboxylic acid tert-butyl ester (0.5 g, 2.52 mmol)), 2-(2-bromoethoxy)tetrahydropyran (0.42 mL, 2.77 mmol) and potassium carbonate (1.2 g, 8.82 mmol) in 4-methylpentan-2-one was stirred under reflux overnight. The resulting mixture was evaporated under reduced pressure and the residue was partitioned between water and dichloromethane. The organic layer was washed with brine, dried (MgSO₄) and evaporated under reduced pressure to yield 5-[2-(tetrahydro-pyran-2-yloxy)ethyl]-2,5-diazabicyclo[2.2.1]heptane-2-carboxylic acid tert-butyl ester (0.80 g, quantitative) as an oil.

b) A mixture of 5-[2-(tetrahydro-pyran-2-yloxy)ethyl]-2,5-diazabicyclo[2.2.1]heptane-2-carboxylic acid tert-butyl ester (0.80 mmol, 2.4 mmol) and aqueous hydrochloric acid (2 mL, 2N) in ethanol (10 mL) was stirred under reflux for one hour and then evaporated under reduced pressure to yield crude (1S,4S)-2-(2,5-Diazabicyclo[2.2.1]hept-2-yl) ethanol, dihydrochloride (0.51 g) as a dark oil which was used in the next step without further purification.

Preparation 37

2-Methyl-2-piperazin-1-ylpropan-1-ol a) A mixture of piperazine-1-carboxylic acid benzyl ester (8.8 g, 40 mmol), 2-bromo-2-methylpropionic acid ethyl ester and potassium carbonate was stirred at 150° C. for 24 h. On cooling, the resulting mixture was partitioned between dichloromethane and water. The organic layer was washed with brine, dried (MgSO₄) and evaporated under reduced pressure to give 4-(1-Ethoxycarbonyl-1-methyl-ethyl)-piperazine-1-carboxylic acid benzyl ester (10.2 g, 77%) as an oil.

b) A solution of 4-(1-ethoxycarbonyl-1-methyl-ethyl)-piperazine-1-carboxylic acid benzyl ester (3.5 g, 10.5 mmol) in 10 mL of dry ether was slowly added to a suspension of lithium aluminium hydride (0.3 g, 105 mmol) in tetrahydrofuran at −15° C. under nitrogen and the resulting mixture was stirred at 0° C. for 3 hours. On cooling, the mixture was treated dropwise with water (0.3 mL), aqueous sodium hydroxyde (0.3 mL, 4N), and water (0.9 mL) and filtered. The filtrate was concentrated under reduced pressure to yield 4-(2-hydroxy-1,1-dimethyl ethyl)piperazine-1-carboxylic acid benzyl ester as a white solid (1.2 g, 41%).

c) A mixture of 4-(2-hydroxy-1,1-dimethylethyl)piperazine-1-carboxylic acid benzyl ester (3.0 g, 10.3 mmol) in methanol (70 mL) and palladium on charcoal (0.5 g, 10%) was hydrogenated at room temperature at 40 p.s.i. overnight. The mixture was filtered through Celite and the filtrate evaporated under reduced pressure to give the title compound (1.55 g, 98%) as a white solid.

δ (DMSO-d6): 0.92 (6H, s), 2.52 (4H, m), 2.75 (4H, m), 3.23 (2H, s), 4.8 (2H, bs).

EXAMPLES

TABLE 2

| Example No | R¹ | R² | R³ | NR⁴R⁵ |
|---|---|---|---|---|
| 1 | H | Et | Et | 4-methylpiperazin-1-yl |
| 2 | H | Et | Et | 4-(2-hydroxyethyl)piperazin-1-yl |
| 3 | H | Et | Pr | pyridin-4-ylamino |
| 4 | H | Et | Pr | 4-methylpiperazin-1-yl |
| 5 | H | Et | Pr | 4-(2-hydroxyethyl)piperazin-1-yl |
| 6 | H | Et | nBu | 4-methylpiperazin-1-yl |
| 7 | H | Et | nBu | bis(2-hydroxyethyl)amino |
| 8 | H | Et | nBu | 4-(2-hydroxyethyl)piperazin-1-yl |
| 9 | H | Et | nBu | 2-(morpholin-4-yl)ethylamino |
| 10 | H | Et | nBu | 4-[2-(2-hydroxyethoxy)ethyl]piperazin-1-yl |
| 11 | H | Pr | Et | morpholin-4-yl |
| 12 | H | Pr | Et | 4-methylpiperazin-1-yl |

TABLE 2-continued

| Example No | R¹ | R² | R³ | NR⁴R⁵ |
|---|---|---|---|---|
| 13 | H | Pr | Et | piperazin-1-yl-ethanol (N-(2-hydroxyethyl)piperazine) |
| 14 | H | Pr | Pr | piperazine |
| 15 | H | Pr | Pr | morpholine |
| 16 | H | Pr | Pr | NH-CH₂CH₂-N(CH₃)₂ |
| 17 | H | Pr | Pr | 4-aminopyridine (NH-pyridin-4-yl) |
| 18 | H | Pr | Pr | 4-methylpiperazine |
| 19 | H | Pr | Pr | 4-hydroxypiperidine |
| 20 | H | Pr | Pr | N(CH₂CH₂OH)₂ |
| 21 | H | Pr | Pr | 4-formylpiperazine |
| 22 | H | Pr | Pr | 4-methyl-1,4-diazepan-1-yl |
| 23 | H | Pr | Pr | 4-ethylpiperazine |
| 24 | H | Pr | Pr | piperidine-4-carboxamide |
| 25 | H | Pr | Pr | piperidine-3-carboxamide |

TABLE 2-continued

| Example No | R¹ | R² | R³ | NR⁴R⁵ |
|---|---|---|---|---|
| 26 | H | Pr | Pr | NH-CH₂CH₂-piperidinyl |
| 27 | H | Pr | Pr | 4-(2-hydroxyethyl)piperazin-1-yl |
| 28 | H | Pr | Pr | NH-CH₂CH₂-morpholin-4-yl |
| 29 | H | Pr | Pr | NH-CH₂CH₂CH₂-morpholin-4-yl |
| 30 | H | Pr | Pr | 4-[2-(2-hydroxyethoxy)ethyl]piperazin-1-yl |
| 31 | H | Pr | nBu | morpholin-4-yl |
| 32 | H | Pr | nBu | 4-methylpiperazin-1-yl |
| 33 | H | nBu | Et | 4-methylpiperazin-1-yl |
| 34 | H | nBu | Et | 4-(2-hydroxyethyl)piperazin-1-yl |
| 35 | H | nBu | Pr | NH-CH₂CH₂-N(CH₃)₂ |
| 36 | H | nBu | Pr | NH-(pyridin-4-yl) |
| 37 | H | nBu | Pr | 4-methylpiperazin-1-yl |
| 38 | H | nBu | Pr | 4-hydroxypiperidin-1-yl |

TABLE 2-continued

| Example No | R¹ | R² | R³ | NR⁴R⁵ |
|---|---|---|---|---|
| 39 | H | nBu | Pr | bis(2-hydroxyethyl)amino |
| 40 | H | nBu | Pr | 4-methyl-1,4-diazepan-1-yl |
| 41 | H | nBu | Pr | 4-ethylpiperazin-1-yl |
| 42 | H | nBu | Pr | 2-(piperidin-1-yl)ethylamino |
| 43 | H | nBu | Pr | 4-(2-hydroxyethyl)piperazin-1-yl |
| 44 | H | nBu | Pr | 2-(morpholin-4-yl)ethylamino |
| 45 | H | nBu | Pr | 3-(morpholin-4-yl)propylamino |
| 46 | H | nBu | Pr | N-methyl-2-(morpholin-4-yl)ethylamino |
| 47 | H | nBu | Pr | 4-[2-(2-hydroxyethoxy)ethyl]piperazin-1-yl |
| 48 | H | nBu | nBu | 4-methylpiperazin-1-yl |
| 49 | H | nBu | nBu | 4-(2-hydroxyethyl)piperazin-1-yl |
| 50 | H | 4-pyridyl-methyl | Pr | 4-methylpiperazin-1-yl |
| 51 | Me | Pr | Pr | N(CH₃)₂ |

TABLE 2-continued

| Example No | R¹ | R² | R³ | NR⁴R⁵ |
|---|---|---|---|---|
| 52 | Me | Pr | Pr | N-methylpiperazine |
| 53 | Me | Pr | Pr | 4-(2-hydroxyethyl)piperazine |
| 54 | Pr | nBu | Pr | N-methylpiperazine |
| 55 | Pr | nBu | Pr | 4-(2-hydroxyethyl)piperazine |
| 56 | Pr | nBu | Pr | 4-[2-(2-hydroxyethoxy)ethyl]piperazine |
| 57 | Bn | Pr | Pr | N-methylpiperazine |
| 58 | H | iBu | Pr | N-methylpiperazine |
| 59 | H | iBu | Pr | N-methyl-1,4-diazepane |
| 60 | H | iBu | Pr | 2-morpholinoethylamino |
| 61 | H | iBu | Pr | 3-morpholinopropylamino |
| 62 | H | iBu | Pr | N-ethylpiperazine |
| 63 | H | iBu | Pr | 4-(2-hydroxyethyl)piperazine |
| 64 | H | iBu | Pr | 4-hydroxypiperidine |

TABLE 2-continued

| Example No | R¹ | R² | R³ | NR⁴R⁵ |
|---|---|---|---|---|
| 65 | H | iBu | Pr | NH-CH₂CH₂-piperidinyl |
| 66 | H | iBu | Pr | NH-CH₂CH₂-N(CH₃)₂ |
| 67 | H | iBu | Pr | morpholinyl |
| 68 | H | iBu | Pr | N(CH₃)-CH₂CH₂-morpholinyl |
| 69 | H | n-Pn | Pr | 4-methylpiperazinyl |
| 70 | H | n-Pn | Pr | 4-methyl-1,4-diazepanyl |
| 71 | H | n-Pn | Pr | NH-CH₂CH₂-morpholinyl |
| 72 | H | n-Pn | Pr | NH-CH₂CH₂CH₂-morpholinyl |
| 73 | H | n-Pn | Pr | 4-ethylpiperazinyl |
| 74 | H | n-Pn | Pr | 4-(2-hydroxyethyl)piperazinyl |
| 75 | H | n-Pn | Pr | 4-hydroxypiperidinyl |
| 76 | H | n-Pn | Pr | NH-CH₂CH₂-piperidinyl |
| 77 | H | n-Pn | Pr | NH-CH₂CH₂-N(CH₃)₂ |

TABLE 2-continued

| Example No | R¹ | R² | R³ | NR⁴R⁵ |
|---|---|---|---|---|
| 78 | H | n-Pn | Pr | morpholine |
| 79 | H | nPr | Et | piperazine |
| 80 | H | nPr | nPr | NH₂ |
| 81 | H | nPr | nPr | HN-CH₂-C≡CH |
| 82 | H | nPr | nPr | HN-CH₂CH₂-N(CH₃)₂ |
| 83 | H | nPr | nPr | (1S,4S)-2,5-diazabicyclo[2.2.1]heptane |
| 84 | H | nPr | nPr | 1,4-diazepane |
| 85 | H | nPr | nPr | (S)-2-methylpiperazine |
| 86 | H | nPr | nPr | (R)-2-methylpiperazine |
| 87 | H | nPr | nPr | 3-(dimethylamino)azetidine |
| 88 | H | nPr | nPr | N-CH₂CH₂CH₂-N(CH₃)₂ |
| 89 | H | nPr | nPr | (1S,4S)-2-methyl-2,5-diazabicyclo[2.2.1]heptane |
| 90 | H | nPr | nPr | 1-ethylpiperazine |
| 91 | H | nPr | nPr | 3-((dimethylamino)methyl)azetidine |
| 92 | H | nPr | nPr | HN-CH₂CH₂-pyrrolidine |

TABLE 2-continued

| Example No | R¹ | R² | R³ | NR⁴R⁵ |
|---|---|---|---|---|
| 93 | H | nPr | nPr | (2,6-dimethylpiperazinyl, trans) |
| 94 | H | nPr | nPr | (2,5-dimethylpiperazinyl) |
| 95 | H | nPr | nPr | N-ethyl-N'-(2-dimethylaminoethyl)amine |
| 96 | H | nPr | nPr | 4-allylpiperazin-1-yl |
| 97 | H | nPr | nPr | octahydropyrrolo[1,2-a]pyrazine |
| 98 | H | nPr | nPr | 4-propylpiperazin-1-yl |
| 99 | H | nPr | nPr | 2,6-dimethyl-4-methylpiperazin-1-yl |
| 100 | H | nPr | nPr | 2-morpholinoethylamino |
| 101 | H | nPr | nPr | 2,2-dimethyl-3-dimethylaminopropylamino |
| 102 | H | nPr | nPr | 5-(2-hydroxyethyl)-2,5-diazabicyclo[2.2.1]heptane |
| 103 | H | nPr | nPr | 3-morpholinopropylamino |

TABLE 2-continued

| Example No | R¹ | R² | R³ | NR⁴R⁵ |
|---|---|---|---|---|
| 104 | H | nPr | nPr | piperazine-N-CH₂CH₂-OCH₃ |
| 105 | H | nPr | nPr | 1,4-diazepane-N-CH₂CH₂-OH |
| 106 | H | nPr | nPr | piperazine-N-CH(CH₃)CH₂OH |
| 107 | H | nPr | nPr | 1-(aminomethyl)-1-(ethylamino)cyclohexane |
| 108 | H | nPr | nPr | piperazine-N-C(CH₃)₂CH₂OH |
| 109 | H | nPr | nPr | piperazine-N-CH₂CF₃ |
| 110 | H | nPr | nPr | 1-(aminomethyl)-1-(ethylamino)cycloheptane |
| 111 | H | nPr | nPr | 1-(aminomethyl)-1-(diethylamino)cyclohexane |
| 112 | H | nPr | nPr | N-methyl-2-(3,4-dimethoxyphenyl)ethylamine |
| 113 | H | nPr | nPr | 1-(aminomethyl)-1-(diethylamino)cycloheptane |

TABLE 2-continued

| Example No | R¹ | R² | R³ | NR⁴R⁵ |
|---|---|---|---|---|
| 114 | H | nPr | nPr | 4-(aminomethyl)-4-phenyl-1-methylpiperidine |
| 115 | H | nPr | nPr | 1-(3-hydroxypropyl)piperazine |
| 116 | H | nPr | nPr | N(CH$_3$)$_2$ |
| 117 | H | nPr | nPr | guanidine (NH–C(=NH)–NH$_2$) |
| 118 | H | nPr | nPr | NH–CH$_2$CH$_2$–OH |
| 119 | H | nPr | nPr | 3-amino-1H-1,2,4-triazole |
| 120 | H | nPr | nPr | N(CH$_3$)–CH$_2$CH$_2$–N(CH$_3$)$_2$ |
| 121 | H | nPr | nPr | NH–CH$_2$–(4-pyridyl) |
| 122 | H | nPr | nPr | NH–CH$_2$CH$_2$–(2-pyridyl) |
| 123 | H | nPr | nPr | NH–(CH$_2$)$_3$–(1-imidazolyl) |
| 124 | H | nPr | nPr | 1-methyl-4-(methylamino)piperidine |
| 125 | H | nPr | nPr | 1-isopropylpiperazine |
| 126 | H | nPr | nPr | N(CH$_3$)(CH$_2$-2-tetrahydrofuryl) |

TABLE 2-continued

| Example No | R¹ | R² | R³ | NR⁴R⁵ |
|---|---|---|---|---|
| 127 | H | nPr | nPr | 2,2,6,6-tetramethyl-4-aminopiperidinyl |
| 128 | H | nPr | nPr | 4-hydroxy-4-((methylamino)methyl)-1-methylpiperidinyl |
| 129 | H | nPr | nPr | 4-(2-ethoxyethyl)piperazinyl |
| 130 | H | nPr | nPr | 4-(trifluoroacetyl)piperazinyl |
| 131 | H | nPr | nPr | N-(1-(aminomethyl)cycloheptyl)acetamide |
| 132 | H | nBu | nPr | 3-hydroxyazetidinyl |
| 133 | H | nBu | nPr | piperazinyl |
| 134 | H | nBu | nPr | 1-methyl-3-(methylamino)azetidinyl |
| 135 | H | nBu | nPr | 3-((dimethylamino)methyl)azetidinyl |
| 136 | H | nBu | nPr | 3-((2-hydroxyethyl)(methyl)amino)azetidinyl |
| 137 | H | nBu | nPr | 4-(1-hydroxypropan-2-yl)piperazinyl |

TABLE 2-continued

| Example No | R¹ | R² | R³ | NR⁴R⁵ |
|---|---|---|---|---|
| 138 | H | nBu | nPr | piperazine-N-C(CH₃)₂-CH₂OH |
| 139 | H | iBu | nPr | N(CH₂CH₂OH)₂ |
| 140 | H | iBu | nPr | 4-methylpiperazin-1-yl-NH |
| 141 | H | iBu | nPr | 4-(2-hydroxyethyl)piperidin-1-yl |
| 142 | H | iBu | nPr | 4-[2-(2-hydroxyethoxy)ethyl]piperazin-1-yl |
| 143 | H | —(CH$_2$)$_2$OCH$_3$ | nPr | N(nPr)(CH₂CH₂OH) |
| 144 | H | —(CH$_2$)$_2$OCH$_3$ | nPr | HN-CH₂CH₂-morpholin-4-yl |
| 145 | H | —(CH$_2$)$_2$OCH$_3$ | nPr | 4-(3-hydroxypropyl)piperazin-1-yl |
| 146 | H | —(CH$_2$)$_2$OCH$_3$ | nPr | HN-(CH₂)₃-morpholin-4-yl |
| 147 | H | nPn | nPr | N(CH₂CH₂OH)₂ |
| 148 | H | nPn | nPr | 4-(2-hydroxyethyl)piperidin-1-yl |

TABLE 2-continued

| Example No | R¹ | R² | R³ | NR⁴R⁵ |
|---|---|---|---|---|
| 149 | H | nPn | nPr | 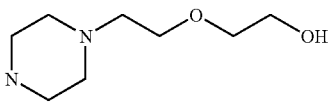 |

Example 1

8-[2-Ethoxy-5-(4-methylpiperazine-1-sulphonyl)phenyl]-6-ethyl-6,9-dihydro-[1,2,4]triazolo[3,4-i]purin-5-one To a mixture of the title compound of Preparation 2 (1.1 g, 2.4 mmol) and triethylamine (0.4 mL, 2.6 mmol) in dichloromethane (50 mL) was added dropwise a solution of 1-methylpiperazine (0.3 mL, 2.6 mmol) in dichloromethane (25 mL) and the resulting mixture was stirred at room temperature overnight. The reaction mixture was diluted with dichloromethane, washed with aqueous solution of sodium bicarbonate and water, dried (MgSO$_4$) and evaporated under reduced pressure. The resulting crude residue on crystallisation from ethanol afforded the title compound (1.1 g, 93%) as a white solid.

m.p. 248° C.

δ (DMSO-d6): 1.38 (3H, t), 1.50 (3H, t), 2.15 (3H, s), 2.40 (4H, m), 2.93 (4H, m), 4.25 (2H, m), 4.40 (2H, m), 7.45 (1H, d), 7.90 (1H, d), 8.24 (1H, s), 9.28 (1H, s), 13.70 (1H, bs).

Example 2

8-{2-Ethoxy-5-[4-(2-hydroxyethyl)piperazine-1-sulphonyl]phenyl}-6-ethyl-6,9-dihydro-[1,2,4]triazolo[3,4-i]purin-5-one Obtained as a white solid (88 %) from the title compound of Preparation 2 and 1-(2-hydroxyethyl)piperazine following the procedure of example 1.

m.p. 230° C.

δ (DMSO-d6): 1.40 (3H, t), 1.50 (3H, t), 2.38 (2H, t), 2.50 (4H, m), 2.90 (4H, m), 3.40 (2H, m), 4.28 (2H, m), 4.40 (3H, m), 7.46 (1H, d), 7.90 (1H, d), 8.26 (1H, s), 9.27 (1H, s), 13.65 (1H, bs).

Example 3

6-Ethyl-8-[2-propoxy-5-(4-pyridylaminosulphonyl)]phenyl-6,9-dihydro-[1,2,4]triazolo[3,4-i]purin-5-one Obtained as a white solid (46%) from the title compound of Preparation 2 and 4-aminopyridine following the procedure of example 1.

m.p. 279° C.

δ (DMSO-d6): 0.98 (3H, t), 1.39 (3H, t), 1.83 (2H, m), 4.19 (4H, m), 6.94 (2H, bs), 7.38 (1H, d), 7.84 (1H, d), 8.04 (2H, bs), 8.39 (1H, s), 9.22 (1H, s).

Example 4

6-Ethyl-8-[5-(4-methylpiperazine-1-sulphonyl)-2-propoxyphenyl]-6,9-dihydro-[1,2,4]triazolo[3,4-i]purin-5-one Obtained as a white solid (61%) from the title compound of Preparation 4 and 1-methylpiperazine following the procedure of example 1.

m.p. 117° C.

δ (DMSO-d6): 1.01 (3H, t), 1.37 (3H, t), 1.86 (2H, m), 2.38 (4H, m), 2.92 (4H, m), 4.26 (4H, m), 7.48 (1H, d), 7.80 (1H, d), 8.21 (1H, s), 9.28 (1H, s), 13.72 (1H, bs)

Example 5

6-Ethyl-8-{2-propoxy-5-[4-(2-hydroxyethyl)piperazine-1-sulphonyl]phenyl}-6,9-dihydro-[1,2,4]triazolo[3,4-i]purin-5-one Obtained as a white solid (86 %) from the title compound of Preparation 4 and 1-(2-hydroxyethyl)piperazine following the procedure of example 1.

m.p. 217° C.

δ (DMSO-d6): 1.0 (3H, t), 1.37 (3H, t), 1.89 (2H, m), 2.36 (2H, t), 2.50 (2H, m), 2.79 (4H, m), 3.40 (2H, m), 4.22 (2H, t), 4.38 (1H, bs), 7.48 (1H, d), 7.82 (1H, d), 8.22 (1H, s), 9.28 (1H, s), 13.70 (1H, bs)

Example 6

6-Ethyl-8-(2-Butoxy-5-[4-(methylpiperazine-1-sulphonyl)phenyl]-6,9-dihydro-[1,2,4]triazolo[3,4-i]purin-5-one Obtained as a white solid (56%) from the title compound of Preparation 6 and 1-methylpiperazine following the procedure of example 1.

m.p. 206° C.

δ (DMSO-d6): 0.94 (3H, t), 1.38 (3H, t), 1.48 (2H, m), 1.84 (2H, m), 2.16 (3H, s), 2.38 (4H, m), 2.94 (4H, m), 4.31 (4H, m), 7.80 (1H, d), 7.81 (1H, d), 8.22 (1H, s), 9.26 (1H, s), 13.71 (1H, bs)

Example 7

4-Butoxy-3-(6-ethyl-5-oxo-6,9-dihydro-5H-[1,2,4]triazolo[3,4-i]purin-8-yl)-N,N-bis-(2-hydroxyethyl)benzenesulfonamide Obtained as a white solid (71%) from the title compound of Preparation 6 and diethanolamine following the procedure of example 1.

m.p. 189° C.

Example 8

6-Ethyl-8-(2-butoxy-5-[4-(2-hydroxyethyl)piperazine-1-sulphonyl]phenyl)-6,9-dihydro-[1,2,4]triazolo[3,4-i]purin-5-one Obtained as a white solid (54%) from the title compound of Preparation 6 and 1-(2-hydroxyethyl)piperazine following the procedure of example 1.

m.p. 235° C.

δ (DMSO-d6): 0.93 (3H, t), 1.37 (3H, t), 1.45 (2H, m), 1.86 (2H, m), 2.38 (2H, t), 2.50 (4H, m), 2.91 (4H, m), 3.42 (2H, m), 4.30 (5H, m), 7.48 (1H, d), 7.80 (1H, d), 8.20 (1H, s), 9.26 (1H, s), 13.72 (1H, bs)

Example 9

4-Butoxy-3-(6-ethyl-5-oxo-6,9-dihydro-5H-[1,2,4]triazolo[3,4-i]purin-8-yl)-N-(2-morpholin-4-ylethyl)benzenesulfonamide Obtained as a white solid (61%) from the title compound of Preparation 6 and N-(2-aminoethyl)morpholine following the procedure of example 1.

m.p. 158° C.

δ (DMSO-d6): 0.93 (3H, m), 1.41 (5H, m), 1.84 (2H, m), 2.30 (6H, m), 2.90 (2H, m), 3.48 (4H, m), 4.30 (4H, m), 7.43 (1H, d), 7.59 (1H, m), 7.88 (1H, d), 8.37 (1H, d), 9.26 (1H, s).

Example 10

8-(2-Butoxy-5-{4-[2-(2-hydroxyethoxy)ethyl]piperazine-1-sulfonyl}phenyl)-6-ethyl-6,9-dihydro-[1,2,4]triazolo[3,4-i]purin-5-one Obtained as a white solid (70%) from the title compound of Preparation 6 and 1-[2-(2-hydroxyethoxy)ethyl]piperazine following the procedure of example 1.

m.p. 108° C.

δ (DMSO-d6): 0.94 (3H, m), 1.42 (5H, m), 1.83 (2H, m), 2.46 (6H, m), 2.91 (4H, m), 3.36 (6H, m), 4.32 (4H, m), 7.47 (1H, d), 7.78 (1H, d), 8.22 (1H, d), 9.27 (1H, s).

Example 11

8-{2-Ethoxy-5-[4-morpholine-1-sulphonyl]phenyl}-6-propyl-6,9-dihydro-[1,2,4]triazolo[3,4-i]purin-5-one Obtained as a white solid (37%) from the title compound of Preparation 8 and morpholine following the procedure of example 1.

m.p. 265° C.

δ (DMSO-d6): 0.95 (3H, t), 1.45 (3H, t), 1.85 (2H, m), 2.90 (4H, m), 3.65 (4H, m), 4.20 (2H, t), 4.40 (2H, c), 7,45 (1H, d), 7,80 (1H, d), 8,22 (1H, s), 9.25 (1H, s), 13,7 (1H, bs)

Example 12

8-[2-Ethoxy-5-(4-methylpiperazine-1-sulphonyl)phenyl]-6-propyl-6,9-dihydro-[1,2,4]triazolo[3,4-i]purin-5-one Obtained as a white solid (68%) from the title compound of Preparation 8 and 1-methylpiperazine following the procedure of example 1.

m.p. 252° C.

δ (DMSO-d6): 1.0 (3H, t), 1.48 (3H, t), 1.88 (2H, m), 2.19 (3H, s), 2.40 (4H, m), 2.94 (4H, m), 4.21 (2H, t), 4.41 (2H, q), 7.48 (1H, d), 7.82 (1H, d), 8.22 (1H, s), 9.28 (1H, s), 13.68 (1H, bs)

Example 13

8-{2-Ethoxy-5-[4-(2-hydroxyethyl)piperazine-1-sulphonyl]phenyl}-6-propyl-6,9-dihydro-[1,2,4]triazolo[3,4-i]purin-5-one Obtained as a white solid (21%) from the title compound of Preparation 8 and 1-(2-hydroxyethyl)piperazine following the procedure of example 1.

m.p. 223° C.

δ (DMSO-d6): 0.98 (3H, t), 1.60 (3H, t), 1.85 (2H, m), 2.38 (2H, t), 2.50 (4H, m), 2.91 (4H, m), 3.41 (2H, m), 4.19 (2H, t), 2.39 (3H, m), 7.46 (1H, d), 7.81 (1H, d), 8.22 (1H, s), 9.28 (1H, s), 13.72 (1H, bs)

Example 14

8-[2-Ethoxy-5-(piperazine-1-sulphonyl)phenyl]-6-propyl-6,9-dihydro-[1,2,4]triazolo[3,4-i]purin-5-one Obtained as a white solid (25%) from the title compound of Preparation 10 and piperazine following the procedure of example 1.

m.p. 230° C.

δ (DMSO-d6): 0.97 (3H, t), 1.00 (3H, t), 1.86 (4H, m), 2.81 (8H, m), 4.19 (2H, t), 4.37 (2H, t), 7.46 (1H, d), 7.78 (1H, d), 8.19 (1H, s), 9.26 (1H, bs)

Example 15

8-[5-(morpholinosulphonyl)-2-propoxyphenyl]-6-propyl-6,9-dihydro-[1,2,4]triazolo[3,4-i]purin-5-one A stirred mixture of the title compound of Preparation 22 (0.22 g, 0.45 mmol) and formic acid (5 mL) was heated under reflux for 2 hours. The resulting solution was concentrated under vacuum and the residue partitioned between dichloromethane and aqueous sodium bicarbonate solution, then the organic phase separated, washed with water, dried (MgSO$_4$) and evaporated under reduced pressure to yield the crude product which was purified by Flash Column Chromatography (SiO$_2$, dichloromethane-methanol 98:2) to give the title compound (0.17 g, 76%) as an off-white solid.

m.p. 169° C.

δ (DMSO-d6): 0.98 (3H, t), 1.02 (3H, t), 1.86 (4H, m), 2.89 (4H, m), 3.61 (4H, m), 4.20 (2H,t), 4.24 (2H, t), 7.45 (1H, d), 7.82 (1H, d), 8.22 (1H, s), 9.28 (1H, s), 13.68 (1H, s)

δ (DMSO-d6): 0.94 (3H, m), 1.39 (5H, m), 1.84 (2H, m), 3.23 (4H, m), 3.56 (4H, m), 4.29 (4H, m), 7.43 (1H, d), 7.89 (1H, d), 9.25 (1H, s).

Example 16

N-(2-Dimethylaminoethyl)-3-(5-oxo-6-propyl-6,9-dihydro-5H-[1,2,4]triazolo[3,4-i]purin-8-yl)-4-propoxybenzenesulphonamide Obtained as a white solid (36%) from the title compound of Preparation 10 and N,N-dimethylethylenediamine following the procedure of example 1.

LRMS: m/z 503 (M+1)$^+$.

δ (DMSO-d6): 0.98 (3H, t), 1.02 (3H, t), 1.86 (4H, m), 2.89 (4H, m), 3.61 (4H, m), 4.20 (2H,t), 4.24 (2H, t), 7.45 (1H, d), 7.82 (1H, d), 8.22 (1H, s), 9.28 (1H, s), 13.68 (1H, s)

Example 17

3-(5-Oxo-6-propyl-6,9-dihydro-5H-[1,2,4]triazolo[3,4-i]purin-8-yl)-4-propoxy-N-pyridin-4-yl-benzenesulphonamide Obtained as a white solid (10%) from the title compound of Preparation 10 and 4-aminopyridine following the procedure of example 1.

m.p. 265° C.

δ (DMSO-d6): 0.98 (3H, t), 1.02 (3H, t), 1.86 (4H, m), 2.89 (4H, m), 3.61 (4H, m), 4.20 (2H,t), 4.24 (2H, t), 7.45 (1H, d), 7.82 (1H, d), 8.22 (1H, s), 9.28 (1H, s), 13.68 (1H, s)

Example 18

8-[5-(4-Methylpiperazinosulphonyl)-2-propoxyphenyl]-6-propyl-6,9-dihydro-[1,2,4]triazolo[3,4-i]purin-5-one Obtained as a white solid (82%) from the title compound of Preparation 19 following the procedure of example 15.

m.p. 272° C.

δ (DMSO-d6): 0.98 (3H, t), 1.00 (3H, t), 1.83 (4H, m), 2.18 (3H, s), 2.38 (4H, m), 2.86 (4H, m), 4.19 (2H, t), 4.28 (2H, t), 7.44 (1H, d), 7.80 (1H, d), 8.19 (1H, s), 9.23 (1H, s), 13.75 (1H, bs)

Example 19

8-[5-(4-Hydroxypiperidine-1-sulphonyl)-2-propoxyphenyl]-6-propyl-6,9-dihydro-[1,2,4]triazolo[3,4-i]purin-5-one Obtained as a white solid (35%) from the title compound of Preparation 10 and 4-hydroxypiperidine following the procedure of example 1.

LRMS: m/z 516 (M+1)$^+$.

δ (DMSO-d6): 0.98 (6H, m), 1.48 (2H, m), 1.74 (2H, m), 1.84 (4H, m), 2.77 (2H, m), 3.16 (2H, m), 3.60 (1H, m), 4.21 (1H, m), 4.68 (1H, s), 7.45 (1H, d), 7.78 (1H, d), 8.20 (1H, s), 9.26 (1H, s), 13.8 (1H, bs)

Example 20

N,N-Bis-(2-hydroxyethyl)-3-(5-oxo-6-propyl-6,9-dihydro-5H-[1,2,4]triazolo[3,4-i]purin-8-yl)-4-propoxybenzenesulphon amide Obtained as a white solid (28%) from the title compound of Preparation 10 and diethanolamine following the procedure of example 1.

LRMS: m/z 520 (M+1)$^+$.

δ (DMSO-d6): 0.97 (6H, m), 1.86 (4H, m), 3.20 (4H, t), 3.54 (4H, t), 4.20 (4H, m), 4.82 (2H, bs), 7.41 (1H, d), 7.83 (1H, d), 8.31 (1H, s), 9.23 (1H, s), 12.0 (1H, bs)

Example 21

4-[3-(5-Oxo-6-propyl-6,9-dihydro-5N-[1,2,4]triazolo[3,4-i]purin-8-yl)-4-propoxybenzenesulphonyl]piperazine-1-carbaldehyde Obtained as a white solid (28%) from the title compound of Preparation 20 following the procedure of example 15.

m.p. 232° C.

δ (DMSO-d6): 0.95 (3H, t), 1.0 (3H, t), 1.86 (4H, m) 2.93 (4H, m), 3.45 (4H, m), 4.20 (2H, t), 4.24 (2H, t), 7.46 (1H, d), 7.80 (1H, d), 7.94 (1H, s), 8.20 (1H, s), 9.26 (1H, s), 13.76 (1H, s)

Example 22

8-[5-(4-Methyl-[1,4]diazepane-1-sulfonyl)-2-propoxyphenyl]-6-propyl-6,9-dihydro-[1,2,4]triazolo[3,4-i]purin,5-one Obtained as a white solid (32%) from the title compound of Preparation 21 following the procedure of example 15.

m.p. 193° C.

δ (DMSO-d6): 0.96 (3H, t), 0.98 (3H, t), 1.8 (6H, m), 2.22 (3H, s), 2.50 (2H, m), 2.58 (2H, m), 3.32 (4H, m), 4.18 (2H, t), 4.26 (2H, t), 7.40 (1H, d), 7.83 (1H, d), 8.22 (1H, s), 9.25 (1H, s)

Example 23

8-[5-(4-Ethylpiperazine-1-sulphonyl)-2-propoxyphenyl]-6-propyl-6,9-dihydro-[1,2,4]triazolo[3,4-i]purin-5-one Obtained as a white solid (48%) from the title compound of Preparation 10 and 1-ethylpiperazine following the procedure of example 1.

LRMS: m/z 529 (M+1)$^+$.

δ (DMSO-d6): 0.97 (9H, m), 1.83 (4H, m), 2.36 (2H, m), 2.45 (2H, m), 2.94 (4H, m), 3.35 (2H, m), 4.19 (2H, t), 4.27 (2H, t), 7.47 (1H, d), 7.80 (1H, d), 8.19 (1H, s), 9.26 (1H, s)

Example 24

1-[3-(5-Oxo-6-propyl-6,9-dihydro-5H-[1,2,4]triazolo[3,4-i]purin-8-yl)-4-propoxybenzenesulphonyl]piperidine-4-carboxylic acid amide Obtained as a white solid (12%) from the title compound of Preparation 10 and isonipecotamide following the procedure of example 1.

m.p. 272° C.

δ (DMSO-d6): 0.96 (3H, t), 0.98 (3H, t), 1.58 (2H, m), 1.6–1.8 (6H, m), 2.07 (1H, m), 2.36 (2H, m), 3.57 (2H, m), 4.19 (2H, t), 4.28 (2H, t), 6.81 (1H, s), 7.20 (1H,s), 7.46 (1H, d), 7.82 (1H, d), 8.20 (1H, s), 9.27 (1H, s), 13.72 (1H, s)

Example 25

1-[3-(5-Oxo-6-propyl-6,9-dihydro-5H-[1,2,4]triazolo [3,4-i]purin-8-yl)-4-propoxybenzenesulphonyl]piperidine-3-carboxylic acid amide Obtained as a white solid (55%) from the title compound of Preparation 10 and nipecotamide following the procedure of example 1.

LRMS: m/z 543 (M+1)$^+$.

δ (DMSO-d6): 0.97 (6H, m), 1.21 (1H, m), 1.50 (1H, m), 1.82 (6H, m)r 2.26 (2H, m), 2.40 (1H, m), 3.62 (2H, m), 4.18 (2H, t), 4.27 (2H, t), 6.95 (1H, s), 7.42 (1H, s), 7.46 (1H, d), 7.80 (1H, d), 8.20 (1H, s), 9.25 (1H, s), 13.75 (1H, s)

Example 26

3-(5-Oxo-6-propyl-6,9-dihydro-5H-[1,2,4]triazolo[3,4-i]purin-8-yl)-N-(2-piperidin-1-ylethyl)-4-propoxy benzenesulphonamide Obtained as a white solid (45%) from the title compound of Preparation 10 and 1-(2-aminoethyl)piperidine following the procedure of example 1.

LRMS: m/z 543 (M+1)$^+$.

δ (DMSO-d6): 9.26 (1H, s), 8.32 (1H, s), 7.83 (1H, d), 7.62 (1H, s), 7.43 (1H, d), 4.21 (4H, m), 2.92 (2H, m), 2.41 (6H, m), 1.86 (4H, m), 1.46 (4H, m), 1.38 (2H, m), 0.97 (6H, m)

Example 27

8-{5-[4-(2-Hydroxyethyl)piperazine-1-sulphonyl]-2-propoxyphenyl}-6-propyl-6,9-dihydro-[1,2,4]triazolo[3,4-i]purin-5-one Obtained as a white solid (41%) from the title compound of Preparation 10 and 1-(2-hydroxyethyl)piperazine following the procedure of example m.p. 194° C.

δ (DMSO-d6): 0.95 (3H, t), 0.99 (3H, t), 1.84 (4H, m), 2.36 (2H, m), 2.50 (4H, m), 2.82 (4H, m), 3.40 (2H, m), 4.18 (2H, t), 4.28 (2H, t), 4.37 (1H, bs), 7.46 (1H, d), 7.80 (1H, d), 8.18 (1H, s), 9.26 (1H, s), 13.76 (1H, bs)

Example 28

N-(2-Morpholin-4-yl-ethyl)-3-(5-oxo-6-propyl-6,9-dihydro-5H-[1,2,4]triazolo[3,4-i]purin-8-yl)-4-propoxybenzene sulphonamide Obtained as a white solid (40%) from the title compound of Preparation 10 and 4-(2-aminoethyl)morpholine following the procedure of example 1.

LRMS: m/z 545 (M+1)$^+$.

δ (DMSO-d6): 0.97 (6H, m), 1.85 (4H, m), 2.28 (6H, m), 2.90 (2H, m), 3.48 (4H, m), 4.23 (4H, m), 7.43 (1H, d), 7.62 (1H, s), 7.90 (1H, d), 8.32 (1H, s), 9.26 (1H, s) 13.60 (1H, bs)

Example 29

N-(3-Morpholin-4-yl-propyl)-3-(5-oxo-6-propyl-6,9-dihydro-5H-[1,2,4]triazolo[3,4-i]purin-8-yl)-4-propoxybenzene sulphonamide Obtained as a white solid (29%) from the title compound of Preparation 10 and 4-(3-aminopropyl)morpholine following the procedure of example 1.

LRMS: m/z 559 (M+1)$^+$.

δ (DMSO-d6): 0.97 (6H, m), 1.86 (4H, m), 2.30 (6H, m), 2.81 (2H, m), 3.51 (4H, m), 4.23 (4H, m), 7.43 (1H, d), 7.63 (1H, s), 7.85 (1H, d), 8.31 (1H, s), 9.25 (1H, s)

Example 30

8-(5-{4-[2-(2-Hydroxyethoxy)ethyl]piperazine-1-sulphonyl}-2-propoxyphenyl)-6-propyl-6,9-dihydro-[1,2,4]triazolo[3,4-i]purin-5-one Obtained as a white solid (60%) from the title compound of Preparation 10 and 1-[2-(2-hydroxyethoxy)ethyl]piperazine following the procedure of example 1.

m.p. 116° C.

δ (DMSO-d6): 1.03 (6H, m), 1.84 (4H, m), 2.45 (6H, m), 2.92 (4H, m), 3.39 (6H, m), 4.21 (4H, m), 4.58 (1H, s), 7.41 (1H, d).

Example 31

8-[2-Butoxy-5-(morpholine-4-sulphonyl)phenyl]-6-propyl-6,9-dihydro-[1,2,4]triazolo[3,4-i]purin-5-one Obtained as a white solid (39%) from the title compound of Preparation 23 following the procedure of example 15.

m.p. 208° C.

δ (DMSO-d6): 0.94 (3H, t), 0.96 (3H, t), 1.48 (2H, m), 1.84 (4H, m)2.93 (4H, m), 3.64 (4h, m), 4.20 (2H, t), 4.31 (2H, t), 7.48 (1H, d), 7.82 (1H, d), 8.20 (1H, s), 9.26 (1H, s), 13.76 (1H, s)

Example 32

8-[5-(2-butoxy-4-methylpiperazinosulphonyl)phenyl]-6-propyl-6,9-dihydro-1,2,4-triazolo[3,4-i]purin-5-one Obtained as a white solid (17%) from the title compound of Preparation 24 following the procedure of example 15.

m.p. 208° C.

δ (DMSO-d6): 0.91 (3H, t), 0.92 (3H, t), 1.43 (2H, m) 1.81 (4H, m), 2.09 (3H, s), 2.36 (4H, m), 2.88 (4H, m), 4.17 (2H, t), 4.26 (2H, t), 7.44 (1H, d), 7.79 (1H, d), 8.17 (1H, s), 9.25 (1H, s)

Example 33

6-Butyl-8-[2-ethoxy-5-(4-methylpiperazine-1-sulphonyl)phenyl]-6,9-dihydro-[1,2,4]triazolo[3,4-i]purin-5-one Obtained as a white solid (72%) from the title compound of Preparation 12 and 1-methylpiperazine following the procedure of example 1.

m.p. 238° C.

δ (DMSO-d6): 0.99 (3H, t), 1.42 (5H, m), 1.82 (2H, m), 2.16 (3H, s), 2.40 (4H, m), 2.92 (4H, m), 4.22 (2H, t), 4.40 (2H, q), 7.44 (1H, d), 7.80 (1H, d), 8.22 (1H, s), 9.24 (1H, s), 13.48 (1H, s)

Example 34

6-Butyl-8-{2-ethoxy-5-[4-(2-hydroxyethyl)piperazine-1-sulphonyl]phenyl}-6,9-dihydro-[1,2,4]triazolo[3,4-i]purin-5-one Obtained as a white solid (45%) from the title compound of Preparation 12 and 1-(2-hydroxyethyl)piperazine following the procedure of example 1.

m.p. 241° C.

δ (DMSO-d6): 0.92 (3H, t), 1.38 (2H, m), 1.41 (3H, t), 1.80 (2H, m), 2.38 (2H, t), 2.48 (4H, m), 2.88 (4H, m), 3.40 (2H, m), 4.21 (2H, t), 4.40 (2H, q), 7.43 (1H, d), 7.80 (1H, d), 8.24 (1H, s), 9.24 (1H, s), 13.68 (1H, s).

Example 35

3-(6-Butyl-5-oxo-6,9-dihydro-5H-[1,2,4]triazolo[3,4-i]purin-8-yl)-N-(2-dimethylaminoethyl)-4-propoxybenzenesulfonamide Obtained as a white solid (71%) from the title compound of Preparation 14 and N,N-dimethylethylenediamine following the procedure of example 1.

m.p. 181° C.

δ (DMSO-d6): 0.96 (6H, m), 1.37 (2H, m), 1.84 (4H, m), 2.08 (6H, s), 2.29 (2H, m), 2.86 (2H, m), 4.25 (4H, m), 7.42 (1H, d), 7.57 (1H, bs), 7.86 (1H, d), 8.34 (1H, d), 9.24 (1H, s).

Example 36

6-Butyl-8-[2-propoxy-5-(4-pyridylaminosulphonyl)]phenyl-6,9-dihydro-[1,2,4]triazolo[3,4-i]purin-5-one Obtained as a white solid (39%) from the title compound of Preparation 14 and 4-aminopyridine following the procedure of example 1.

m.p. 282° C.

δ (DMSO-d6): 0.97 (6H, m), 1.40 (2H, m), 1.82 (4H, m), 4.22 (4H, m), 6.97 (2H, bs), 7.38 (1H, d), 7.89 (1H, d), 8.03 (2H, bs), 8.39 (1H, s), 9.23 (1H, s)

Example 37

6-Butyl-8-(2-propoxy-5-[4-(methylpiperazine-1-sulphonyl)phenyl]-6,9-dihydro-[1,2,4]triazolo[3,4-i]purin-5-one Obtained as a white solid (78%) from the title compound of Preparation 14 and 1-methylpiperazine following the procedure of example 1.

m.p. 220° C.

δ (DMSO-d6): 0.83 (6H, m), 1.36 (2H, m), 1.80 (4H, m) 2.12 (3H, s), 2.38 (4H, m), 2.92 (4H, m), 4.23 (4H, m), 7.45 (1H, d), 7.79 (1H, d), 8.19 (1H, s), 9.21 (1H, s), 13.69 (1H, bs).

Example 38

6-Butyl-8-[5-(4-hydroxypiperidine-1-sulfonyl)-2-propoxyphenyl]-6,9-dihydro-[1,2,4]triazolo[3,4-i]purin-5-one Obtained as a white solid (70%) from the title compound of Preparation 14 and 4-hydroxypiperidine following the procedure of example 1.

m.p. 262° C.

δ (DMSO-d6): 0.97 (6H, m), 1.41 (4H, m), 1.81 (6H, m), 2.78 (2H, m), 3.16 (2H, m), 3.55 (1H, bs), 4.24 (4H, m), 4.67 (1H, d), 7.45 (1H, d), 7.80 (1H, d), 8.23 (1H, d), 9.25 (1H, s).

Example 39

3-(6-Butyl-5-oxo-6,9-dihydro-5H-[1,2,4]triazolo[3,4-i]purin-8-yl)-N,N-bis-(2-hydroxyethyl)-4-propoxybenzenesulfonamide Obtained as a white solid (50%) from the title compound of Preparation 14 and diethanolamine following the procedure of example 1.

m.p. 202° C.

δ (DMSO-d6): 0.97 (6H, m), 1.38 (2H, m), 1.82 (4H, m), 3.19 (4H, m), 3.54 (4H, m), 4.25 (4H, m), 4.84 (2H, m), 7.42 (1H, d), 7.87 (1H, d), 8.29 (1H, d), 9.25 (1H, s), 13.69 (1H, s).

Example 40

6-Butyl-8-[5-(4-methyl-[1,4]diazepane-1-sulfonyl)-2-propoxyphenyl]-6,9-dihydro-[1,2,4]triazolo[3,4-i]purin-5-one Obtained as a white solid (39%) from the title compound of Preparation 14 and 1-methylhomopiperazine following the procedure of example 1.

m.p. 282° C.

d (CDCl$_3$): 1.03 (3H, t), 1.14 (3H, t), 1.47 (2H, m), 1.8–2.2 (6H, m), 2.38 (3H, s), 2.68 (4H, m), 3.46 (4H, m), 4.38 (4H, m), 7.19 (1H, d), 7.86 (1H, d), 8.79 (1H, s), 8.96 (1H, s).

Example 41

6-Butyl-8-{2-propoxy-5-[4-(ethylpiperazine-1-sulphonyl)phenyl]-6,9-dihydro[1,2,4]triazolo[3,4-i]purin-5-one Obtained as a white solid (61%) from the title compound of Preparation 14 and 1-ethylpiperazine following the procedure of example 1.

m.p. 208° C.

d (CDCl$_3$): 0.98 (6H, m), 1.16 (3H, t), 1.48 (2H, m) 1.91 (2H, m), 2.04 (2H, m), 2.42 (2H, q), 2.54 (4H, m), 3.13 (4H, m), 4.37 (4H, m), 7.09 (1H, d), 7.82 (1H, d), 8.77 (1H, s), 8.97 (1H, s).

Example 42

3-(6-Butyl-5-oxo-6,9-dihydro-5H-[1,2,4]triazolo[3,4-i]purin-8-yl)-N-(2-piperidin-1-ylethyl)-4-propoxybenzenesulfonamide Obtained as a white solid (60%) from the title compound of Preparation 14 and 1-(2-aminoethyl)piperidine following the procedure of example 1.

m.p. 186° C.

$\delta$ (DMSO-d6): 0.96 (6H, m), 1.33 (8H, m), 1.83 (4H, m), 2.28 (6H, m), 2.87 (2H, m), 4.24 (4H, m), 7.41 (1H, d), 7.51 (1H, m), 7.85 (1H, d), 8.33 (1H, d), 9.23 (1H, s).

Example 43

6-Butyl-8-(2-propoxy-5-[4-(2-hydroxyethyl)piperazine-1-sulphonyl]phenyl}-6,9-dihydro[1,2,4]triazolo[3,4-i]purin-5-one Obtained as a white solid (81%) from the title compound of Preparation 14 and 1-(2-hydroxyethyl)piperazine following the procedure of example 1.

m.p. 242° C.

$\delta$ (DMSO-d6): 0.96 (3H, t), 1.0 (3H, t), 1.38 (2H, m), 1.86 (4H, m), 2.37 (2H, t), 2.50 (4H, m), 2.92 (4H, m), 3.43 (2H, m), 4.26 (4H, m), 4.37 (1H, bs), 7.47 (1H, d), 7.80 (1H, d), 8.21 (1H, s), 9.25 (1H, s), 13.70 (1H, bs).

Example 44

3-(6-Butyl-5-oxo-6,9-dihydro-5H-[1,2,4]triazolo[3,4-i]purin-8-yl)-N-(2-morpholin-4-ylethyl)-4-propoxybenzenesulfonamide Obtained as a white solid (72%) from the title compound of Preparation 14 and 4-(2-aminoethyl)morpholine following the procedure of example 1.

m.p. 192° C.

$\delta$ (DMSO-d6): 0.95 (6H, m), 1.38 (2H, m), 1.83 (4H, m), 2.28 (6H, m), 2.90 (2H, m), 3.46 (4H, m), 4.25 (4H, m), 7.42 (1H, d), 7.59 (1H, m), 7.87 (1H, d), 8.33 (1H, d), 9.25 (1H, s).

Example 45

3-(6-Butyl-5-oxo-6,9-dihydro-5H-[1,2,4]triazolo[3,4-i]purin-8-yl)-N-(3-morpholin-4-ylpropyl)-4-propoxybenzenesulfonamide Obtained as a white solid (65%) from the title compound of Preparation 14 and 4-(3-aminopropyl)morpholine following the procedure of example 1.

m.p. 174° C.

$\delta$ (DMSO-d6): 0.96 (6H, m), 1.38 (2H, m), 1.52 (2H, m), 1.84 (4H, m), 2.21 (6H, m), 2.81 (2H, m), 3.47 (4H, m), 4.25 (4H, m), 7.43 (1H, d), 7.63 (1H, m), 7.84 (1H, d) 8.32 (1H, d), 9.25 (1H, s)

Example 46

3-(6-Butyl-5-oxo-6,9-dihydro-5H-[1,2,4]triazolo[3,4-i]purin-8-yl)-N-methyl-N-(2-morpholin-4-ylethyl)-4-propoxybenzenesulfonamide Obtained as a white solid (65%) from the title compound of Preparation 14 and 4-(3-aminopropyl)morpholine following the procedure of example 1.

m.p. 170° C.

$\delta$ (DMSO-d6): 0.97 (6H, m), 1.38 (2H, m), 1.82 (4H, m), 2.46 (6H, m), 2.76 (3H, s), 3.12 (2H, m), 3.51 (4H, m), 4.24 (4H, m), 7.43 (1H, d), 7.84 (1H, d), 8.26 (1H, d9, 9.25 (1H, s).

Example 47

6-Butyl-8-(5-{4-[2-(2-hydroxyethoxy)ethyl]piperazine-1-sulfonyl}-2-propoxyphenyl)-6,9-dihydro-[1,2,4]triazolo[3,4-i]purin-5-one Obtained as a white solid (64%) from the title compound of Preparation 14 and 1-[2-(2-hydroxyethoxy)ethyl]piperazine following the procedure of example 1.

m.p. 143° C.

$\delta$ (DMSO-d6): 0.83 (6H, m), 1.27 (2H, m), 1.68 (4H, m), 2.35 (6H, m), 2.75 (4H, m), 3.23 (6H, m), 4.11 (4H, m), 7.31 (1H, d), 7.63 (1H, d), 8.06 (1H, s), 9.10 (1H, s).

Example 48

6-Butyl-8-(2-butoxy-5-[4-(methylpiperazine-1-sulphonyl)phenyl]-6,9-dihydro[1,2,4]triazolo[3,4-i]purin-5-one Obtained as a white solid (62%) from the title compound of Preparation 16 and 1-methylpiperazine following the procedure of example 1.

m.p. 201° C.

$\delta$ (DMSO-d6): 0.98 (6H, m), 1.4 (4H, m), 1.8 (4H, m) 2.19 (3H, s), 2.4 (4H, m), 2.90 (4H, m), 4.25 (2H, t), 4.30 (2H, t), 7.45 (1H, d), 7.79 (1H, d), 8.20 (1H, s), 9.25 (1H, s), 13.65 (1H, bs).

Example 49

6-Butyl-8-(2-butoxy-5-[4-(2-hydroxyethyl)piperazine-1-sulphonyl]phenyl}-6,9-dihydro[1,2,4]triazolo[3,4-i]purin-5-one Obtained as a white solid (66%) from the title compound of Preparation 16 and 1-methylpiperazine following the procedure of example 1.

m.p. 218° C.

$\delta$ (DMSO-d6): 0.95 (6H, m), 1.20 (4H, m), 1.85 (4H, m), 2.40 (2H, t), 2.51 (4H, m), 2.92 (4H, m), 3.40 (2H, m), 4.25 (5H, m), 7.48 (1H, d), 7.80 (1H, d), 8.24 (1H, s), 9.28 (1H, s), 13.65 (1H, bs).

Example 50

8-[5-(4-Methylpiperazine-1-sulfonyl)-2-propoxyphenyl]-6-pyridin-2-ylmethyl-6,9-dihydro-[1,2,4]triazolo[3,4-i]purin-5-one Obtained as a white solid (82%) from the title compound of Preparation 26 and 1-methylpiperazine following the procedure of example 1.

m.p. 227° C.

δ (DMSO-d6): 0.93 (3H, m), 1.80 (2H, m), 2.13 (3H, s), 2.35 (4H, m), 2.87 (4H, m), 4.24 (2H, m), 5.53 (2H, m), 7.28 (1H, m), 7.44 (2H, m), 7.75 (2H, m), 8.09 (1H, d), 8.45 (1H, d), 9.31 (1H, s).

Example 51

8-[5-(N,N-Dimethylaminosulphonyl)-2-propoxyphenyl]-3-methyl-6-propyl-6,9-dihydro-[1,2,4]triazolo[3,4-i]purin-2,6-dione Obtained as a white solid (65%) from the title compound of Preparation 18 and dimethylamine following the procedure of example 1.

m.p. 226° C.

δ (DMSO-d6): 0.96 (3H, t), 0.98 (3H, t), 1.84 (4H, m), 2.62 (6H, s), 2.78 (3H, s), 4.16 (2H, t), 4.24 (2H, t), 7.44 (1H, d), 7.81 (1H, d), 8.21 (1H, s), 13.59 (1H, s)

Example 52

3-Methyl-8-[5-(4-methylpiperazine-1-sulphonyl)-2-propoxyphenyl]-6-propyl-6,9-dihydro-[1,2,4]triazolo[3,4-i]purin-5-one Obtained as a white solid (62%) from the title compound of Preparation 18 and 1-methylpiperazine following the procedure of example 1.

m.p. 226° C.

δ (DMSO-d6): 0.96 (3H, t), 0.99 (3H, t), 1.82 (4H, m), 2.16 (3H, s), 2.37 (4H, m), 2.78 (3H, s), 2.84 (4H, m), 4.14 (2H, t), 4.28 (2H, t), 7.44 (1H, d), 7.78 (1H, d), 8.19 (1H, s), 13.60 (1H, s)

Example 53

8-{5-[4-(2-hydroxyethyl)piperazine-1-sulphonyl]-2-propoxyphenyl}-3-methyl-6-propyl-6,9-dihydro-[1,2,4]triazolo[3,4-i]purin-5-one Obtained as a white solid (61%) from the title compound of Preparation 18 and 1-(2-hydroxyethyl)piperazine following the procedure of example 1.

m.p. 199° C.

δ (DMSO-d6): 0.92 (3H, t), 0.98 (3H, t), 1.82 (4H, m), 2.38 (2H, t), 2.46 (4H, m), 2.77 (3H, s), 2.84 (4H, m), 3.39 (2H, m), 4.16 (2H, t), 4.24 (2H, t), 4.37 (1H, t), 7.43 (1H, d), 7.79 (1H, d), 8.18 (1H, s), 13.60 (1H, s)

Example 54

6-Butyl-8-[5-(4-methylpiperazine-1-sulfonyl)-2-propoxyphenyl]-3-propyl-6,9-dihydro-[1,2,4]triazolo[3,4-i]purin-5-one Obtained as a cream solid (77%) from the title compound of Preparation 28 and 1-methylpiperazine following the procedure of example 1.

m.p. 206° C.

δ (DMSO-d6): 0.97 (9H, m), 1.37 (2H, m), 1.81 (6H, m), 2.14 (3H, s), 2.37 (4H, m), 2.92 (4H, m), 3.19 (2H, m), 4.17 (2H, m), 4.26 (2H, m), 7.45 (1H, d), 7.79 (1H, d), 8.19 (1H, d), 13.59 (1H, bs).

Example 55

6-Butyl-8-{5-[4-(2-hydroxyethyl)piperazine-1-sulfonyl]-2-propoxyphenyl}-3-propyl-6,9-dihydro-[1,2,4]triazolo[3,4-i]purin-5-one Obtained as a pale yellow solid (83%) from the title compound of Preparation 28 and 1-(2-hydroxyethyl)piperazine following the procedure of example 1.

m.p. 193° C.

δ (DMSO-d6): 0.97 (9H, m), 1.37 (2H, m), 1.81 (6H, m), 2.14 (3H, s), 2.37 (4H, m), 2.92 (4H, m), 3.19 (2H, m), 4.17 (2H, m), 4.26 (2H, m), 7.45 (1H, d), 7.79 (1H, d), 8.19 (1H, d), 13.59 (1H, bs).

Example 56

6-Butyl-8-(5-{4-[2-(2-hydroxyethoxy)ethyl]piperazine-1-sulfonyl}-2-propoxyphenyl)-3-propyl-6,9-dihydro-[1,2,4]triazolo[3,4-i]purin-5-one Obtained as a pale yellow solid (81%) from the title compound of Preparation 28 and 1-[2-(2-hydroxyethoxy)ethyl]piperazine following the procedure of example 1.

m.p. 144° C.

δ (DMSO-d6): 0.97 (9H, m), 1.38 (2H, m), 1.81 (6H, m) 2.46 (6H, m), 2.91 (4H, m), 3.19 (2H, m), 3.37 (6H, m), 4.18 (2H, m), 4.27 (2H, m), 7.45 (1H, d), 7.80 (1H, d), 8.19 (1H, d).

Example 57

3-Benzyl-8-[5-(4-methylpiperazine-1-sulfonyl)-2-propoxyphenyl]-6-propyl-6,9-dihydro-[1,2,4]triazolo[3,4-i]purin-5-one To a mixture of the title compound of Preparation 19 (0.5 g, 1.0 mmol) and triethylamine (0.2 mL, 1.3 mmol) in dichloromethane (40 mL) was added phenylacetyl chloride (0.17 mL, 1.3 mmol) and the resulting mixture was stirred at room temperature for 24 hours, then evaporated under reduced pressure. Toluene (40 ml) and a catalytic amount of p-toluenesulphonic acid was added to the residue and the resulting mixture refluxed for 2 hours using a Dean-Stark apparatus, then evaporated under reduced pressure to yield the crude product which was purified by Flash Column Chromatography (SiO$_2$, dichloromethane-ethanol-aq. ammonia 100:4:0.5) to yield the title compound (0.11 g, 18%) as a white solid.

m.p. 202° C.

δ (DMSO-d6): 0.92 (3H, t), 0.96 (3H, t), 1.81 (4H, m), 2.14 (3H, s), 2.37 (4H, m), 2.92 (4H, m), 4.12 (2H, t), 4.25 (2H, t), 4.65 (2H, s), 7.30 (5H, m), 7.45 (1H, d), 7.77 (1H, d), 8.17 (1H, s)

Example 58

6-Isobutyl-8-[5-(4-methylpiperazine-1-sulfonyl)-2-propoxyphenyl]-6,9-dihydro-[1,2,4]triazolo[3,4-i]purin-5-one Obtained as a white solid (51%) from the title compound of Preparation 30 and 1-methylpiperazine following the procedure of example 1.

LRMS: m/z 528 (M+1)+.

δ (DMSO-d6): 0.94 (9H, m), 1.83 (2H, m), 2.18 (3H, s), 2.40 (1H, m), 2.45 (4H, m), 2.93 (4H, m), 4.02 (2H, d), 4.24 (2H, t), 7.44 (1H, d), 7.78 (1H, dd), 8.16 (1H, d), 9.24 (1H, s), 13.7 (1H, bs).

Example 59

6-Isobutyl-8-[5-(4-methyl-[1,4]diazepane-1-sulfonyl)-2-propoxyphenyl]-6,9-dihydro-[1,2,4]triazolo[3,4-i]purin-5-one Obtained as a white solid (41%) from the title compound of Preparation 30 and 1-methylhomopiperazine following the procedure of example 1.

LRMS: m/z 542 (M+1)+.

δ (DMSO-d6): 1.02 (9H, m), 1.88 (5H, m), 2.48 (1H, m), 2.51 (2H, m), 2.86 (4H, m), 3.32 (4H, m), 4.05 (2H, d), 4.26 (2H, t), 7.43 (1H, d), 7.86 (1H, dd), 8.24 (1H, s), 9.27 (1H, s).

Example 60

3-(6-Isobutyl-5-oxo-6,9-dihydro-5H-[1,2,4]triazolo[3,4-i]purin-8-yl)-N-(2-morpholin-4-ylethyl)-4-propoxybenzenesulfonamide Obtained as a white solid (49%) from the title compound of Preparation 30 and 4-(2-aminoethyl)morpholine following the procedure of example 1.

LRMS: m/z 558 (M+1)+.

δ (DMSO-d6): 1.00 (9H, m), 1.85 (2H, m), 2.35 (6H, m), 2.94 (2H, m), 3.40 (4H, m), 4.06 (2H, d), 4.26 (2H, t), 7.43 (1H, d), 7.70 (1H, bs), 7.88 (1H, dd), 8.30 (1H, d), 9.26 (1H, s), 13.65 (1H, bs).

Example 61

3-(6-Isobutyl-5-oxo-6,9-dihydro-5H-[1,2,4]triazolo[3,4-i]purin-8-yl)-N-(3-morpholin-4-ylpropyl)-4-propoxybenzenesulfonamide Obtained as a white solid (29%) from the title compound of Preparation 30 and 4-(3-aminopropyl)morpholine following the procedure of example 1.

LRMS: m/z 572 (M+1)+.

δ (DMSO-d6): 1.09 (9H, m), 1.59 (2H, m), 1.85 (2H, m) 2.40 (6H, m), 2.81 (2H, m), 3.37 (4H, m), 4.06 (2H, d), 4.26 (2H, t), 7.43 (1H, d), 7.70 (1H, t), 7.85 (1H, dd), 8.30 (1H, d), 9.26 (1H, s), 13.5 (1H, bs).

Example 62

8-[5-(4-Ethylpiperazine-1-sulfonyl)-2-propoxyphenyl]-6-isobutyl-6,9-dihydro-[1,2,4]triazolo[3,4-i]purin-5-one Obtained as a white solid (52%) from the title compound of Preparation 30 and 1-ethylpiperazine following the procedure of example 1.

LRMS: m/z 542 (M+1)+.

δ (DMSO-d6): 1.00 (12H, m), 1.86 (2H, m), 2.45 (7H, m), 2.97 (4H, m), 4.05 (2H, d), 4.27 (2H, t), 7.47 (1H, d), 7.81 (1H, dd), 8.20 (1H, d), 9.27 (1H, s), 13.7 (1H, bs).

Example 63

8-{5-[4-(2-Hydroxyethyl)piperazine-1-sulfonyl]-2-propoxyphenyl}-6-isobutyl-6,9-dihydro-[1,2,4]triazolo[3,4-i]purin-5-one Obtained as a white solid (42%) from the title compound of Preparation 30 and 1-(2-hydroxyethyl)piperazine following the procedure of example 1.

LRMS: m/z 558 (M+1)+.

δ (DMSO-d6): 1.00 (9H, m), 1.86 (2H, m), 2.36 (1H, m), 2.64 (4H, m), 2.99 (4H, m), 3.35 (4H, m), 4.05 (2H, d), 4.27 (2H, t), 4.56 (1H, bs), 7.47 (1H, d), 7.81 (1H, dd), 8.19 (1H, d), 9.27 (1H, s), 13.8 (1H, bs).

Example 64

8-[5-(4-Hydroxypiperidine-1-sulfonyl)-2-propoxyphenyl]-6-isobutyl-6,9-dihydro-[1,2,4]triazolo[3,4-i]purin-5-one Obtained as a white solid (53%) from the title compound of Preparation 30 and 4-hydroxypiperidine following the procedure of example 1.

LRMS: m/z 529 (M+1)+.

δ (DMSO-d6): 0.95 (9H, m), 1.45 (2H, m), 1.79 (4H, m), 2.36 (1H, m), 2.77 (2H, m), 3.17 (2H, m), 3.55 (1H, m), 4.04 (2H, d), 4.26 (2H, t), 4.69 (1H, d), 7.45 (1H, d), 7.80 (1H, dd), 8.20 (1H, d), 9.26 (1H, s), 13.76 (1H, s).

Example 65

3-(6-Isobutyl-5-oxo-6,9-dihydro-5H-[1,2,4]triazolo[3,4-i]purin-8-yl)-N-(2-piperidin-1-ylethyl)-4-propoxybenzenesulfonamide Obtained as a white solid (60%) from the title compound of Preparation 30 and 1-(2-aminoethyl)piperidine following the procedure of example 1.

LRMS: m/z 556 (M+1)+.

δ (DMSO-d6): 1.00 (9H, m), 1.41 (2H, m), 1.55 (4H, m), 1.87 (2H, m), 2.38 (1H, m), 2.65 (4H, m), 3.03 (4H, m), 4.06 (2H, d), 4.27 (2H, t), 7.44 (1H, d), 7.89 (1H, dd), 7.82 (1H, bs), 8.31 (1H, d), 9.26 (1H, s).

Example 66

N-(2-Dimethylaminoethyl)-3-(6-isobutyl-5-oxo-6,9-dihydro-5H-[1,2,4]triazolo[3,4-i]purin-8-yl)-4-propoxybenzenesulfonamide Obtained as a white solid (43%) from the title compound of Preparation 30 and N,N'-dimethylethylenediamine following the procedure of example LRMS: m/z 516 (M+1)+.

δ (DMSO-d6): 0.95 (9H, m), 1.84 (2H, m), 2.33 (1H, m), 2.33 (6H, s), 2.61 (2H, m), 2.94 (2H, m), 4.03 (2H, d), 4.23 (2H, t), 7.41 (1H, d), 7.82 (1H, bs), 7.86 (1H, dd) 8.28 (1H, d), 9.23 (1H, s)

Example 67

6-Isobutyl-8-[5-(morpholinosulphonyl)-2-propoxyphenyl]-6,9- dihydro-[1,2,4]triazolo[3,4-i]purin-5-one Obtained as a white solid (53%) from the title compound of Preparation 30 and morpholine following the procedure of example 1.

LRMS: m/z 515 (M+1)+.

δ (DMSO-d6): 0.96 (9H, m), 1.83 (2H, m), 2.33 (1H, m), 2.88 (4H, m), 3.62 (4H, m), 4.02 (2H, d), 4.24 (2H, t), 7.45 (1H, d), 7.78 (1H, d), 8.16 (1H, s), 9.23 (1H, s), 13.77 (1H, s).

Example 68

3-(6-Isobutyl-5-oxo-6,9-dihydro-5H-[1,2,4]triazolo[3,4-i]purin-8-yl)-N-methyl-N-(2-morpholin-4-ylethyl)-4-propoxybenzenesulfonamide Obtained as a white solid (53%) from the title compound of Preparation 30 and 4-[2-(N-methylamino)ethyl]morpholine following the procedure of example 1.

LRMS: m/z 572 (M+1)+.

δ (DMSO-d6): 0.94 (9H, m), 1.84 (2H, m), 2.41 (6H, m), 2.74 (3H, s), 3.11 (2H, m), 3.52 (4H, m), 4.01 (2H, d), 4.23 (2H, t), 7.41 (1H, d), 7.83 (1H, d), 8.22 (1H, s), 9.23 (1H, s).

Example 69

8-[5-(4-Methylpiperazine-1-sulfonyl)-2-propoxyphenyl]-6-pentyl-6,9-dihydro-[1,2,4]triazolo[3,4-i]purin-5-one Obtained as a white solid (35%) from the title compound of Preparation 32 and 1-methylpiperazine following the procedure of example 1.

LRMS: m/z 542 (M+1)+.

δ (DMSO-d6): 0.85 (3H, t), 0.97 (3H, t), 1.33 (4H, m), 1.83 (4H, m), 2.25 (3H, s), 2.48 (4H, m), 2.96 (4H, m), 4.22 (4H, m), 7.45 (1H, d), 7.78 (1H, d), 8.20 (1H, s), 9.24 (1H, s), 13.7 (1H, bs).

Example 70

8-[5-(4-Methyl-[1,4]diazepane-1-sulfonyl)-2-propoxyphenyl]-6-pentyl-6,9-dihydro-[1,2,4]triazolo[3,4-i]purin-5-one Obtained as a white solid (40%) from the title compound of Preparation 32 and 1-methylhomopiperazine following the procedure of example 1.

LRMS: m/z 556 (M+1)+.

δ (DMSO-d6): 0.89 (3H, t), 1.02 (3H, t), 1.37 (4H, m), 1.85 (7H, m), 2.50 (2H, m), 2.98 (4H, m), 3.32 (4H, m), 4.23 (4H, m), 7.44 (1H, d), 7.86 (1H, dd), 8.27 (1H, d), 9.26 (1H, s).

Example 71

N-(2-Morpholin-4-ylethyl)-3-(5-oxo-6-pentyl-6,9-dihydro-5H-[1,2,4]triazolo[3,4-i]purin-8-yl)-4-propoxybenzenesulfonamide Obtained as a white solid (32%) from the title compound of Preparation 32 and 4-(2-aminoethyl)morpholine following the procedure of example 1.

LRMS: m/z 572 (M+1)+.

δ (DMSO-d6): 0.90 (3H, t), 0.98 (3H, t), 1.36 (4H, m), 1.86 (4H, m), 2.41 (6H, m), 2.94 (2H, m), 3.53 (4H, m), 4.25 (4H, m), 7.43 (1H, d), 7.68 (1H, bs), 7.88 (1H, dd), 8.33 (1H, d), 8.26 (1H, s), 13.65 (1H, bs).

Example 72

N-(3-Morpholin-4-ylpropyl)-3-(5-oxo-6-pentyl-6,9-dihydro-5H-[1,2,4]triazolo[3,4-i]purin-8-yl)-4-propoxybenzenesulfonamide Obtained as a white solid (38%) from the title compound of Preparation 32 and 4-(3-aminopropyl)morpholine following the procedure of example 1.

LRMS: m/z 586 (M+1)+.

δ (DMSO-d6): 0.87 (3H, t), 0.95 (3H, t), 1.37 (4H, m), 1.61 (2H, m), 1.85 (4H, m), 2.44 (6H, m), 2.81 (2H, m), 3.38 (4H, m), 4.25 (4H, m), 7.44 (1H, d), 7.69 (1H, bs), 7.85 (1H, dd), 8.32 (1H, d), 9.26 (1H, s), 13.6 (1H, bs).

Example 73

8-[5-(4-Ethylpiperazine-1-sulfonyl)-2-propoxyphenyl]-6-pentyl-6,9-dihydro-[1,2,4]triazolo[3,4-i]purin-5-one Obtained as a white solid (35%) from the title compound of Preparation 32 and 1-ethylpiperazine following the procedure of example 1.

LRMS: m/z 556 (M+1)+.

δ (DMSO-d6): 0.90 (3H, t), 1.00 (6H, m), 1.38 (4H, m), 1.85 (4H, m), 2.49–3.07 (10H, m), 4.22 (2H, t), 4.29 (2H, t), 7.48 (1H, d), 7.81 (1H, dd), 8.23 (1H, d), 9.27 (1H, s), 13.75 (1H, bs).

Example 74

8-{5-[4-(2-Hydroxyethyl)piperazine-1-sulfonyl]-2-propoxyphenyl}-6-pentyl-6,9-dihydro-[1,2,4]triazolo[3,4-i]purin-5-one Obtained as a white solid (33%) from the title compound of Preparation 32 and 1-(2-hydroxyethyl)piperazine following the procedure of example 1.

LRMS: m/z 572 (M+1)+.

δ (DMSO-d6): 0.88 (3H, t), 1.00 (3H, t), 1.36 (4H, m), 1.88 (4H, m), 2.46 (4H, m), 2.70 (4H, m), 3.36 (4H, m), 4.28 (4H, m), 4.46 (1H, bs), 7.48 (1H, d), 7.80 (1H, d), 8.22 (1H, s), 9.27 (1H, s), 13.8 (1H, bs).

Example 75

8-[5-(4-Hydroxypiperidine-1-sulfonyl)-2-propoxyphenyl]-6-pentyl-6,9-dihydro-[1,2,4]triazolo[3,4-i]purin-5-one Obtained as a white solid (53%) from the title compound of Preparation 32 and 4-hydroxypiperidine following the procedure of example 1.

LRMS: m/z 543 (M+1)+.

δ (DMSO-d6): 0.88 (3H, t), 1.00 (6H, m), 1.42 (6H, m), 1.82 (6H, m), 2.77 (2H, m), 3.17 (2H, m), 3.54 (1H, m), 4.26 (4H, m), 4.69 (1H, s), 7.46 (1H, d), 7.80 (1H, dd), 8.23 (1H, d), 9.26 (1H, s), 13.7 (1H, s).

Example 76

3-(5-Oxo-6-pentyl-6,9-dihydro-5H-[1,2,4]triazolo[3,4-i]purin-8-yl)-N-(2-piperidin-1-ylethyl)-4-propoxybenzenesulfonamide Obtained as a white solid (55%) from the title compound of Preparation 32 and 1-(2-aminoethyl)piperidine following the procedure of example 1.

LRMS: m/z 579 (M+1)+.

δ (DMSO-d6): 0.88 (3H, t), 0.98 (3H, t), 1.37 (6H, m), 1.60 (4H, m), 1.85 (4H, m), 2.60–3.43 (8H, m), 4.25 (4H, m), 7.45 (1H, d), 7.89 (1H, dd), 7.82 (1H, bs), 8.33 (1H, d), 9.26 (1H, s).

Example 77

N-(2-Dimethylaminoethyl)-3-(5-oxo-6-pentyl-6,9-dihydro-5H-[1,2,4]triazolo[3,4-i]purin-8-yl)-4-propoxybenzenesulfonamide Obtained as a white solid (38%) from the title compound of Preparation 32 and N,N'-dimethylethylenediamine following the procedure of example LRMS: m/z 530 (M+1)+.

δ (DMSO-d6): 0.88 (3H, t), 0.99 (4H, m), 1.35 (4H, m), 1.85 (4H, m), 2.44 (1H, m), 2.44 (6H, s), 2.74 (2H, m), 2.99 (2H, m), 4.22 (4H, m), 7.45 (1H, d), 7.89 (1H, dd), 8.34 (1H, d), 9.26 (1H, s).

Example 78

8-[5-(Morpholinosulphonyl)-2-propoxyphenyl]-6-pentyl-6,9-dihydro-[1,2,4]triazolo[3,4-i]purin-5-one Obtained as a white solid (30%) from the title compound of Preparation 32 and morpholine following the procedure of example 1.

LRMS: m/z 529 (M+1)+.

δ (DMSO-d6): 0.90 (3H, t), 0.99 (3H, t), 1.37 (4H, m), 1.84 (4H, m), 2.89 (4H, m), 3.64 (4H, m), 4.22 (2H, t), 4.29 (2H, t), 7.49 (1H, d), 7.81 (1H, d), 8.22 (1H, s), 9.26 (1H, s), 13.75 (1H, bs).

Example 79

8-[2-Ethoxy-5-(piperazine-1-sulfonyl)phenyl]-6-propyl-6,9-dihydro-[1,2,4]triazolo[3,4-i]purin-5-one Obtained as a white solid (45%) from the title compound of Preparation 4 and piperazine following the procedure of example 1.

m.p. 196° C.

δ (DMSO-d6): 0.95 (3H, t), 1.45 (3H, t), 1.84 (2H, m), 2.76 (4H, m), 2.82 (4H, m), 4.19 (2H, t), 4.40 (2H, t), 7.45 (1H, d), 7.77 (1H, d), 8.21 (1H, s), 9.24 (1H, s).

Example 80

3-(5-Oxo-6-propyl-6,9-dihydro-5H-[1,2,4]triazolo[3,4-i]purin-8-yl)-4-propoxybenzenesulfonamide Obtained as a white solid (26%) from the title compound of Preparation 10 and ammonia following the procedure of example 1.

m.p. 275° C.

δ (DMSO-d6): 0.96 (6H, m), 1.85 (4H, m), 4.19 (t,2H), 4.26 (2H, t), 7.40 (2H, s), 7.41 (1H, d), 7.87 (1H, d), 8.36 (1H, s), 9.26 (1H, s), 13.6 (1H, s).

Example 81

3-(5-Oxo-6-propyl-6,9-dihydro-5H-[1,2,4]triazolo[3,4-i]purin-8-yl)-4-propoxy-N-prop-2-ynylbenzenesulfonamide Obtained as a white solid (41%) from the title compound of Preparation 10 and propargylamine following the procedure of example 1.

m.p. 251° C.

δ (DMSO-d6): 0.97 (6H, m), 1.85 (4H, m), 3.06 (1H, s), (3.71 (2H, s), 4.23 (4H, m), 7.42 (1H, d), 7.87 (1H, d), 8.33 (1H, s), 9.26 (1H, s), 13.6 (1H, s).

Example 82

N-(2-Dimethylaminoethyl)-3-(oxopropyl-6,9-dihydro-5H-[1,2,4]triazolo[3,4-i]purin-8-yl)-4-propoxybenzenesulfonamide Obtained as a white solid (45%) from the title compound of Preparation 10 and N,N-dimethylethylenediamine following the procedure of example 1.

m.p. 193° C.

δ (DMSO-d6): 0.96 (3H, t), 0.99 (3H, t), 1.86 (4H, m), 2.08 (6H, s), 2.29 (2H, t), 2.86 (2H, m), 4.20 (2H, t), 4.27 (2H, t), 7.42 (1H, d), 7.59 (1H, bs), 7.86 (1H, d), 8.32 (1H, s), 9.25 (1H, s).

Example 83

8-{5-[(1S,4S)-(2,5-Diazabicyclo[2.2.1]hept-2-yl) sulfonyl]-2-propoxyphenyl}-6-propyl-6,9-dihydro-[1,2,4]triazolo[3,4-i]purin-5-one Obtained as a white solid (22%) from the title compound of Preparation 10 and tert-butyl (1S,4S)-(−)-2,5-diazabicyclo[2.2.1]heptane-2-carboxylate following the procedure of example 1 and further deprotection in a 1:1 mixture of trifluoroacetic acid and dichloromethane.

m.p. 153° C.

δ (DMSO-d6): 0.98 (7H, m), 1.40 (1H, d), 1.85 (4H, m), 2.83 (1H, d), 2.88 (1H, d), 3.11 (1H, d), 3.19 (1H, d), 3.63 (1H, d), 4.22 (4H, m), 4.34 (1H, s), 4.92 (1H, bs), 7.39 (1H, d) 7.85 (1H, d), 8.29 (1H, s), 9.19 (1H,s)

Example 84

8-[5-([1,4]Diazepane-1-sulfonyl)-2-propoxyphenyl]-6-propyl-6,9-dihydro-[1,2,4]triazolo[3,4-i]purin-5-one Obtained as a white solid (59%) from the title compound of Preparation 10 and homopiperazine following the procedure of example 1.

m.p. 208° C.

δ (DMSO-d6): 0.95 (3H, t), 1.02 (3H, t), 1.72 (2H, m), 1.85 (4H, m), 2.80 (2H, t), 2.85 (2H, t), 3.27 (4H, m), 4.20 (4H, m), 7.38 (1H, d), 7.79 (1H, d), 8.27 (1H, s), 9.20 (1H, s).

Example 85

8-[5-((R)-3-Methylpiperazine-1-sulfonyl)-2-propoxyphenyl]-6-propyl-6,9-dihydro-[1,2,4]triazolo[3,4-i]purin-5-one Obtained as a white solid (80%) from the title compound of Preparation 10 and (R)-(−)-2-methylpiperazine following the procedure of example 1.

m.p. 156° C.

δ (DMSO-d6): 0.93 (3H, d), 0.98 (3H, t), 1.00 (3H, t), 1.83 (4H, m), 2.15 (1H, m), 2.70 (2H, m), 2.90 (1H, m), 3.41 (4H, m), 4.18 (2H, t), 4.26 (2H, t), 7.45 (1H, d), 7.78 (1H, d), 8.19 (1H, s), 9.25 (1H, s).

Example 86

8-[5-((S)-3-Methylpiperazine-1-sulfonyl)-2-propoxyphenyl]-6-propyl-6,9-dihydro-[1,2,4]triazolo[3,4-i]purin-5-one Obtained as a white solid (85%) from the title compound of Preparation 10 and (S)-(−)-2-methylpiperazine following the procedure of example 1.

m.p. 163° C.

δ (DMSO-d6): 0.93 (3H, d), 0.98 (3H, t), 1.00 (3H, t), 1.83 (4H, m), 2.15 (1H, m), 2.70 (2H, m), 2.90 (1H, m), 3.41 (4H, m), 4.18 (2H, t), 4.26 (2H, t), 7.45 (1H, d), 7.78 (1H, d), 8.19 (1H, s), 9.25 (1H, s)

Example 87

8-[5-(3-Dimethylaminoazetidine-1-sulfonyl)-2-propoxyphenyl]-6-propyl-6,9-dihydro-[1,2,4]triazolo[3,4-i]purin-5-one Obtained as a white solid (82%) from the title compound of Preparation 10 and azetidin-3-yldimethylamine following the procedure of example 1.

m.p. 213° C.

δ (DMSO-d6): 0.95 (3H, t), 1.01 (3H, t), 1.84 (4H, m), 2.97 (1H, m), 3.36 (6H, s), 3.45 (2H, t), 3.78 (2H, t), 4.19 (2H, t), 4.29 (2H, t), 7.49 (1H, d), 7.88 (1H, d), 8.25 (1H, s), 9.27 (1H, s), 13.79 (1H, s).

Example 88

N-(3-Dimethylaminopropyl)-3-(oxopropyl-6,9-dihydro-5H-[1,2,4]triazolo[3,4-i]purin-8-yl)-4-propoxybenzenesulfonamide Obtained as a white solid (69%) from the title compound of Preparation 10 and N,N-dimethyl-1,3-propanediamine following the procedure of example 1.

m.p. 197° C.

δ (DMSO-d6): 0.94 (3H, t), 0.97 (3H, t), 1.49 (2H, m), 1.82 (4H, m), 2.07 (6H, s), 2.21 (2H, t), 2.76 (2H, t), 4.17 (2H, t), 4.23 (2H, t), 7.40 (1H, d), 7.65 (1H, bs), 7.81 (1H, d), 8.30 (1H, s), 9.22 (1H, s).

Example 89

8-[5-((1S,4S)-5-Methyl-2,5-diazabicyclo[2.2.1]heptane-2-sulfonyl)-2-propoxyphenyl]-6-propyl-6,9-dihydro-[1,2,4]triazolo[3,4-i]purin-5-one A mixture of the title compound of Example 83 (0.51 g, 1.0 mmol), formaldehyde (0.5 mL, 6.2 mmol, 37%) and formic acid (0.3 mL) was stirred at 80° C. for 2 h. The reaction mixture was concentrated under reduced pressure, diluted with dichloromethane, washed with aqueous solution of sodium bicarbonate and water, dried (MgSO4) and evaporated under reduced pressure. The resulting crude residue was purified by Flash Column Chromatography (SiO2, dichloromethane-ethanol-ammonium hydroxide 140:8:1) to give the title compound (0.22 g, 42%) as a white solid.

m.p. 194° C.

δ (DMSO-d6): 0.98 (7H, m), 1.60 (1H, d), 1.85 (4H, m), 2.24 (3H, s), 2.54 (1H, d), 2.70 (1H, d), 2.99 (1H, d), 3.32 (s, 1H), 3.39 (1H, d), 4.23 (5H, m), 7.44 (1H, d), 7.89 (1H, d), 8.30 (1H, s), 8.24 (1H, s).

Example 90

8-[5-(4-Ethylpiperazine-1-sulfonyl)-2-propoxyphenyl]-6-propyl-6,9-dihydro-[1,2,4]triazolo[3,4-i]purin-5-one Obtained as a white solid (66%) from the title compound of Preparation 10 and N-ethylpiperazine following the procedure of example 1.

m.p. 192° C.

δ (DMSO-d6): 0.96 (9H, m), 1.84 (4H, m), 2.30 (2H, q), 2.43 (4H, m), 2.93 (4H, m), 4.19 (2H, t), 4.27 (2H, t), 7.47 (1H, d), 7.80 (1H, d), 8.20 (1H, s), 9.25 (1H, s).

Example 91

8-[5-(3-Dimethylaminomethylazetidine-1-sulfonyl)-2-propoxyphenyl]-6-propyl-6,9-dihydro-[1,2,4]triazolo[3,4-i]purin-5-one Obtained as a white solid (51%) from the title compound of Preparation 10 and the title compound of Preparation 35 following the procedure of example 1.

m.p. 172° C.

δ (DMSO-d6): 1.01 (6H,m), 1.87 (4H, m), 2.00 (6H, s), 2.10 (2H, d), 2.59 (1H, m), 3.37 (2H, dd), 3.84 (2H, dd), 4.20 (2H, t), 4.30 (2H, t), 7.51 (1H, d), 7.89 (1H, d), 8.29 (1H, s), 9.26 (1H, s).

Example 92

3-(5-Oxo-6-propyl-6,9-dihydro-5H-[1,2,4]triazolo[3,4-i]purin-8-yl)-4-propoxy-N-(2-pyrrolidin-1-ylethyl)benzenesulfonamide Obtained as a white solid (56%) from the title compound of Preparation 10 and 1-(2-aminoethyl)pyrrolidine following the procedure of example 1.

m.p. 198° C.

δ (DMSO-d6): 0.96 (3H, t), 0.99 (3H, t), 1.61 (4H, m), 1.87 (4H, m), 2.4–2.5 (6H, m), 2.88 (2H, t), 4.20 (2H, t), 4.26 (2H, t), 7.42 (1H, d), 7.66 (1H, bs), 7.86 (1H, d), 8.32 (1H, s), 9.25 (1H, s).

Example 93

8-[5-((3R,5S)-3,5-Dimethylpiperazine-1-sulfonyl)-2-propoxyphenyl]-6-propyl-6,9-dihydro-[1,2,4]triazolo[3,4-i]purin-5-one Obtained as a white solid (83%) from the title compound of Preparation 10 and cis-2,6-dimethylpiperazine following the procedure of example 1.

m.p. 200° C.

δ (DMSO-d6): 0.93 (6H, d), 1.00 (3H, t), 1.03 (3H, t), 1.6–1.9 (6H, m), 2.77 (2H, m), 3.50 (2H, m), 4.18 (2H, t), 4.26 (2H, t), 7.45 (1H, d), 7.78 (1H, d), 8.20 (1H, s), 9.25 (1H, s).

Example 94

8-[5-((2RS,5SR)-2,5-Dimethylpiperazine-1-sulfonyl)-2-propoxyphenyl]-6-propyl-6,9-dihydro-[1,2,4]triazolo[3,4-i]purin-5-one Obtained as a white solid (28%) from the title compound of Preparation 10 and trans-2,5-dimethylpiperazine following the procedure of example 1.

m.p. 117° C.

δ (DMSO-d6): 1.02 (9H, m), 1.18 (3H, d), 1.85 (4H, m), 2.47 (1H, m), 1.8–3.1 (3H, m), 3.45 (2H, m), 4.18 (2H, t), 4.2 (2H, t), 7.43 (1H, d), 7.81 (1H, d), 8.29 (1H, s) 9.25 (1H, s).

Example 95

N-(2-Dimethylaminoethyl)-N-ethyl-3-(5-oxo-6-propyl-6,9-dihydro-5H-[1,2,4]triazolo[3,4-i]purin-8-yl)-4-propoxybenzenesulfonamide Obtained as a white solid (34%) from the title compound of Preparation 10 and N,N-dimethyl-N'-ethylethylenediamine following the procedure of example 1.

m.p. 105° C.

δ (DMSO-d6): 0.99 (6H, m), 1.05 (3H, t), 1.85 (4H, m), 2.16 (6H, s), 2.41 (2H, t), 3.21 (4H, m), 4.19 (2H, t), 4.26 (2H, t), 4.41 (1H, d), 7.87 (1H, d), 8.30 (1H, s), 9.25 (1H, s).

Example 96

8-[5-(4-Allylpiperazine-1-sulfonyl)-2-propoxyphenyl]-6-propyl-6,9-dihydro-[1,2,4]triazolo[3,4-i]purin-5-one Obtained as a white solid (65%) from the title compound of Preparation 10 and 1-allyl-piperazine following the procedure of example 1.

m.p. 187° C.

δ (DMSO-d6): 0.96 (6H, m), 1.85 (4H, m), 2.43 (4H, m), 2.92 (6H, m), 4.19 (2H, t), 4.27 (2H, t), 5.11 (2H, m), 5.69 (1H, m), 7.47 (1H, d), 7.80 (1H, d), 8.19 (1H, s), 9.27 (1H, s), 13.76 (1H, bs).

Example 97

8-{5-[(S)-(Hexahydropyrrolo[1,2-a]pyrazin-2-yl)sulfonyl]-2-propoxyphenyl}-6-propyl-6,9-dihydro-[1,2,4]triazolo[3,4-i]purin-5-one Obtained as a white solid (65%) from the title compound of Preparation 10 and (S)-octahydropyrrolo[1,2-a]pyrazine following the procedure of example 1.

m.p. 180° C.

δ (DMSO-d6) 0.99 (6H, m), 1.21 (1H, m), 1.5–2.2 (11H, m), 2.37 (1H, t), 2.8–3.0 (2H, m), 3.60 (1H, d), 3.75 (1H, d), 4.19 (2H, t), 4.27 (2H, t), 7.42 (1H, d), 7.82 (1H, d), 8.22 (1H, s), 9.25 (1H, s), 13.71 (1H, bs).

Example 98

8-[2-Propoxy-5-(4-propylpiperazine-1-sulfonyl)phenyl]-6-propyl-6,9-dihydro-[1,2,4]triazolo[3,4-i]purin-5-one Obtained as a white solid (67%) from the title compound of Preparation 10 and 1-propylpiperazine following the procedure of example 1.

m.p. 192° C.

δ (DMSO-d6): 0.80 (3H, t), 0.98 (6H, m), 1.36 (2H, m), 1.82 (4H, m), 2.21 (2H, t), 2.42 (4H, m), 2.91 (4H, m), 4.19 (2H, t), 4.27 (2H, t), 7.46 (1H, s), 7.79 (1H, d), 8.19 (1H, s), 9.27 (1H, s).

Example 99

8-[2-Propoxy-5-((3R,5S)-3,4,5-trimethylpiperazine-1-sulfonyl)phenyl]-6-propyl-6,9-dihydro-[1,2,4]triazolo[3,4-i]purin-5-one Obtained as a white solid (69%) from the title compound of Preparation 93 following the procedure of example 89.
m.p. 120° C.
δ (DMSO-d6): 1.00 (12H, m), 1.8–2.3 (6H, m), 2.10 (3H, s), 3.48 (2H, d), 4.19 (2H, t), 4.27 (2H, t), 7.46 (1H, d), 7.80 (1H, d), 8.20 (1H, s), 9.26 (1H, s).

Example 100

N-(2-Morpholin-4-ylethyl)-3-(5-oxo-6-propyl-6,9-dihydro-5H-[1,2,4]triazolo[3,4-i]purin-8-yl)-4-propoxybenzenesulfonamide Obtained as a white solid (66%) from the title compound of Preparation 10 and 4-(2-aminoethyl)morpholine following the procedure of example 1.
m.p. 191° C.
δ (CDCl$_3$): 1.07 (3H, t), 1.13 (3H, t), 1.95 (2H, m) 2.04 (2H, m), 2.31 (4H, m), 2.47 (2H, t), 3.08 (2H, m), 3.60 (4H, m), 4.36 (4H, m), 5.68 (1H, bs), 7.18 (1H, d), 7.95 (1H, d), 8.89 (1H, s), 8.97 (1H, s), 11.65 (1H, bs).

Example 101

N-(3-Dimethylamino-2,2-dimethylpropyl)-3-(oxo-propyl-6,9-dihydro-5H-[1,2,4]triazolo[3,4-i]purin-8-yl)-4-propoxybenzenesulfonamide Obtained as a white solid (76%) from the title compound of Preparation 10 and N,N,2,2-tetramethyl-1,3-propanediamine following the procedure of example 1.
m.p. 178° C.
δ (DMSO-d6): 0.81 (6H, s), 0.99 (3H, t), 1.01 (3H, t), 1.88 (4H, m), 2.09 (2H, s), 2.19 (6H, s), 2.61 (2H, s), 4.23 (4H, m), 7.42 (1H, d), 7.55 (1H, bs), 7.86 (1H, d), 8.34 (1H, s), 9.24 (1H, s).

Example 102

8-{5-[(1S,4S)-5-(2-Hydroxyethyl)-2,5-diazabicyclo[2.2.1]heptane-2-sulfonyl]-2-propoxyphenyl}-6-propyl-6,9-dihydro-[1,2,4]triazolo[3,4-i]purin-5-one Obtained as a white solid (67%) from the title compound of Preparation 10 and the title compound of Preparation 36 following the procedure of example 1.
m.p. 183° C.
δ (DMSO-d6): 0.86 (1H, d), 0.96 (3H, t), 1.00 (3H, t), 1.54 (1H, d), 1.86 (4H, m), 2.57 (1H, d), 2.82 (1H, d), 2.97 (1H, d), 3.38 (4H, m), 4.24 (5H, m), 7.44 (1H, d), 7.90 (1H, d), 8.29 (1H, s), 9.27 (1H, s).

Example 103

N-(3-Morpholin-4-ylpropyl)-3-(5-oxo-6-propyl-6,9-dihydro-5H-[1,2,4]triazolo[3,4-i]purin-8-yl)-4-propoxybenzenesulfonamide Obtained as a white solid (62%) from the title compound of Preparation 10 and N-(3-aminopropyl)morpholine following the procedure of example 1.
m.p. 195° C.
δ (DMSO-d6): 0.96 (3H, t), 0.98 (3H, t), 1.52 (2H, m), 1.86 (4H, m), 2.22 (6H, m), 2.80 (2H, m), 3.48 (4H, m), 4.20 (2H, t), 4.26 (2H, t), 7.43 (1H, d), 7.65 (1H, t), 7.84 (1H, d), 8.32 (1H, s), 9.26 (1H, s), 13.58 (1H, bs).

Example 104

8-{5-[4-(2-Methoxyethyl)piperazine-1-sulfonyl]-2-propoxyphenyl}-6-propyl-6,9-dihydro-[1,2,4]triazolo[3,4-i]purin-5-one Obtained as a white solid (67%) from the title compound of Preparation 10 and 1-(2methoxyethyl)piperazine following the procedure of example 1.
m.p. 177° C.
δ (DMSO-d6): 0.96 (3H, t), 1.01 (3H, t), 1.86 (4H, m), 2.59 (6H, m), 2.91 (4H, m), 3.17 (3H, s), 3.35 (2H, t), 4.19 (2H, t), 4.27 (2H, t), 7.47 (1H, d), 7.78 (1H, d), 8.19 (1H, s), 9.27 (1H, s).

Example 105

8-{5-[4-(2-Hydroxyethyl)-[1,4]diazepane-1-sulfonyl]-2-propoxyphenyl}-6-propyl-6,9-dihydro-[1,2,4]triazolo[3,4-i]purin-5-one Obtained as a white solid (67%) from the title compound of Preparation 10 and 2-(1,4-diazepan-1-yl)ethan-1-ol following the procedure of example 1.
m.p. 193° C.
δ (DMSO-d6): 0.98 (6H, m), 1.72 (2H, m), 1.87 (4H, m), 2.63 (2H, t), 2.72 (2H, m), 3.35 (10H, m), 4.23 (4H, m), 7.42 (1H, d), 7.83 (1H, d), 8.25 (1H, s), 9.26 (1H, s).

Example 106

8-{5-[4-(2-Hydroxy-1-methylethyl)piperazine-1-sulfonyl]-2-propoxyphenyl}-6-propyl-6,9-dihydro-[1,2,4]triazolo[3,4-i]purin-5-one Obtained as a white solid (65%) from the title compound of Preparation 10 and 2-piperazin-1-ylpropan-1-ol following the procedure of example 1.
m.p. 216° C.
δ (DMSO-d6): 0.86 (3H, d), 0.95 (3H, t), 0.98 (3H, t), 1.85 (4H, m), 2.56 (4H, m), 2.89 (4H, m), 3.20 (1H, m), 3.39 (2H, m), 4.19 (2H, t), 4.27 (2H, t), 7.46 (1H, d), 7.79 (1H, d), 8.18 (1H, s), 9.25 (1H, s).

Example 107

N-(1-Ethylaminocyclohexylmethyl)-3-(5-oxo-6-propyl-6,9-dihydro-5H-[1,2,4]triazolo[3,4-i]purin-8-yl)-4-propoxybenzenesulfonamide Obtained as a white solid (71%) from the title compound of Preparation 10 and (1-aminomethylcyclohexyl)ethylamine following the procedure of example 1.
m.p. 201° C.
δ (DMSO-d6): 0.96 (9H, m), 1.34 (8H, m), 1.48 (2H, m), 1.84 (4H, m), 2.35 (2H, m), 2.72 (2H, s), 4.20 (4H, m), 7.37 (1H, d), 7.82 (1H, d), 8.36 (1H, s), 9.24 (1H, s).

Example 108

8-{5-[4-(2-Hydroxy-1,1-dimethylethyl)piperazine-1-sulfonyl]-2-propoxyphenyl}-6-propyl-6,9-dihydro-[1,2,4]triazolo[3,4-i]purin-5-one Obtained as a white solid (85%) from the title compound of Preparation 10 and the title compound of Preparation 37 following the procedure of example 1.

m.p. 223° C.

δ (DMSO-d6): 0.88 (6H, s), 0.93 (3H, t), 1.01 (3H, t), 1.86 (4H, m), 2.63 (4H, m), 2.87 (4H, m), 3.20 (2H, bs), 3.34 (1H, bs), 4.20 (2H, t), 4.27 (2H, t), 7.47 (1H, d), 7.76 (1H, d), 8.19 (1H, s), 9.25 (1H, s).

Example 109

8-{2-Propoxy-5-[4-(2,2,2-trifluoroethyl)piperazine-1-sulfonyl]phenyl}-6-propyl-6,9-dihydro-[1,2,4]triazolo[3,4-i]purin-5-one Obtained as a white solid (36%) from the title compound of Preparation 10 and 1-(2,2,2-trifluoroethyl) piperazine following the procedure of example 1.

m.p. 202° C.

δ (DMSO-d6): 0.88 (6H, s), 0.93 (3H, t), 1.01 (3H, t), 1.86 (4H, m), 2.63 (4H, m), 2.87 (4H, m), 3.20 (2H, bs), 3.34 (1H, bs), 4.20 (2H, t), 4.27 (2H, t), 7.47 (1H, d), 7.76 (1H, d), 8.19 (1H, s), 9.25 (1H, s).

Example 110

N-(1-Ethylaminocycloheptylmethyl)-3-(5-oxo-6-propyl-6,9-dihydro-5H-[1,2,4]triazolo[3,4-i]purin-8-yl)-4-propoxybenzenesulfonamide Obtained as a white solid-(53%) from the title compound of Preparation 10 and (1-aminomethyl cycloheptyl)ethylamine following the procedure of example 1.

m.p. 203° C.

δ (DMSO-d6): 0.95 (3H, t), 1.00 (3H, t), 1.2–1.6 (12H, m), 1.86 (4H, m), 2.35 (2H, m), 2.68 (2H, m), 4.19 (2H, t), 4.22 (2H, t), 7.38 (1H, d), 7.82 (1H, d), 8.36 (1H, s), 9.19 (1H, s).

Example 111

N-(1-Diethylaminocyclohexylmethyl)-3-(5-oxo-6-propyl-6,9-dihydro-5H-[-1,2,4]triazolo[3,4-i]purin-8-yl)-4-propoxybenzenesulfonamide Obtained as a white solid (35%) from the title compound of Preparation 10 and (1-aminomethylcyclohexyl)diethylamine following the procedure of example 1.

m.p. 192° C.

δ (DMSO-d6): 1.0 (12H, m), 1.34 (10H, m), 1.83 (4H, m), 2.47 (4H, m), 3.06 (2H, s), 4.22 (4H, m), 7.39 (1H, d), 7.85 (1H, d), 8.31 (1H, s), 9.23 (1H, s).

Example 112

N-[2-(3,4-Dimethoxyphenyl)ethyl]-N-methyl-3-(5-oxo-6-propyl-6,9-dihydro-5H-[1,2,4]triazolo[3,4-i]purin-8-yl)-4-propoxybenzenesulfonamide Obtained as a white solid (42%) from the title compound of Preparation 10 and 2-(3,4-dimethoxyphenyl)-N-methyl-ethylamine following the procedure of example 1.

m.p. 92° C.

δ (DMSO-d6): 0.91 (3H, t), 0.99 (3H, t), 1.84 (4H, m), 2.72 (5H, m), 3.21 (2H, t), 3.33 (3H, s), 3.70 (3H, s), 4.15 (2H, t), 4.25 (2H, t), 6.74 (1H, d), 6.82 (1H, s), 6.84 (1H, d), 7.41 (1H, d), 7.80 (1H, d), 8.23 (1H, s), 9.25 (1H, s), 13.70 (1H, bs).

Example 113

N-(1-Diethylaminocycloheptylmethyl)-3-(5-oxo-6-propyl-6,9-dihydro-5H-[1,2,4]triazolo[3,4-i]purin-8-yl)-4-propoxybenzenesulfonamide Obtained as a white solid (30%) from the title compound of Preparation 10 and (1-aminomethylcycloheptyl) diethylamine following the procedure of example 1.

m.p. 171° C.

δ (DMSO-d6): 1.0 (12H, m), 1.49 (12H, m), 1.84 (4H, m), 2.50 (4H, m), 3.05 (2H, s), 4.21 (4H, m), 7.38 (1H, d), 7.84 (1H, d), 8.31 (1H, s), 9.22 (1H, s).

Example 114

N-(1-Methyl-4-phenylpiperidin-4-ylmethyl)-3-(5-oxo-6-propyl-6,9-dihydro-5H-[1,2,4]triazolo[3,4-i]purin-8-yl)-4-propoxybenzenesulfonamide Obtained as a white solid (54%) from the title compound of Preparation 10 and 4-aminomethyl-1-methyl-4-phenylpiperidine following the procedure of example 1.

m.p. 213° C.

δ (DMSO-d6): 0.95 (3H, t), 0.99 (3H, t), 1.80 (6H, m), 2.04 (4H, m), 2.10 (3H, s), 2.51 (2H, bs), 2.82 (2H, d), 7.0–7.5 (7H, m), 7.73 (1H, d), 8.23 (1H, s), 9.22 (1H, s).

Example 115

8-{5-[4-(3-Hydroxypropyl)piperazine-1-sulfonyl]-2-propoxyphenyl}-6-propyl-6,9-dihydro-[1,2,4]triazolo[3,4-i]purin-5-one To a mixture of the title compound of Preparation 10 (40 mg, 0.09 mmol) and polymer bound morpholine (65 mg, 2.75 mmol/g based on nitrogen analysis) in dichloromethane (3 mL) was added 3-piperazin-1-ylpropan-1-ol (14.1 mg, 0.098 mmol) and the resulting mixture was stirred at room temperature overnight. The reaction mixture was filtered and the filtrate was evaporated under reduced pressure. The residue was triturated with diethyl ether and the precipitate was collected by filtration and dried under vacuum to yield the title compound (41 mg, 82%) as a white solid.

ESI/MS m/e: 559 ([M+H]$^+$, $C_{25}H_{34}N_8O_5S$)

Retention Time (min.): 11.7

Examples 116–131

N,N-Dimethyl-3-(5-oxo-6-propyl-6,9-dihydro-5H-[1,2,4]triazolo[3,4-i]purin-8-yl)-4-propoxybenzenesulfonamide (116)

N-{1-[3-(5-Oxo-6-propyl-6,9-dihydro-5H-[1,2,4]triazolo[3,4-i]purin-8-yl)-4-propoxyphenyl]sulfonylguanidine (117)

N-(2-Hydroxyethyl)-3-(5-oxo-6-propyl-6,9-dihydro-5H-[1,2,4]triazolo[3,4-i]purin-8-yl)-4-propoxybenzenesulfonamide (118)

3-(5-Oxo-6-propyl-6,9-dihydro-5H-[1,2,4]triazolo[3,4-i]purin-8-yl)-4-propoxy-N-(1H-[1,2,4]triazol-3-yl)benzenesulfonamide (119)

N-(2-Dimethylaminoethyl)-N-methyl-3-(oxopropyl-6,9-dihydro-5H-[1,2,4]triazolo[3,4-i]purin-8-yl)-4-propoxybenzenesulfonamide (120)

3-(5-Oxo-6-propyl-6,9-dihydro-5H-[1,2,4]triazolo[3,4-i]purin-8-yl)-4-propoxy-N-pyridin-4-ylmethylbenzenesulfonamide (121)

3-(5-Oxo-6-propyl-6,9-dihydro-5H-[1,2,4]triazolo[3,4-i]purin-8-yl)-4-propoxy-N-(2-pyridin-2-ylethyl)benzenesulfonamide (122)

N-(3-Imidazol-1-ylpropyl)-3-(5-oxo-6-propyl-6,9-dihydro-5H-[1,2,4]triazolo[3,4-i]purin-8-yl)-4-propoxybenzenesulfonamide (123)

N-Methyl-N-(1-methylpiperidin-4-yl)-3-(5-oxo-6-propyl-6,9-dihydro-5H-[1,2,4]triazolo[3,4-i]purin-8-yl)-4-propoxybenzenesulfonamide (124)

8-[5-(4-Isopropylpiperazine-1-sulfonyl)-2-propoxyphenyl]-6-propyl-6,9-dihydro-[1,2,4]triazolo[3,4-i]purin-5-one (125)

N-Ethyl-3-(5-oxo-6-propyl-6,9-dihydro-5H-[1,2,4]triazolo[3,4-i]purin-8-yl)-4-propoxy-N-(tetrahydrofuran-2-ylmethyl)benzenesulfonamide (126)

3-(5-Oxo-6-propyl-6,9-dihydro-5H-[1,2,4]triazolo[3,4-i]purin-8-yl)-4-propoxy-N-(2,2,6,6-tetramethylpiperidin-4-yl)benzenesulfonamide (127)

N-(4-Hydroxy-1-methylpiperidin-4-ylmethyl)-N-methyl-3-(5-oxo-6-propyl-6,9-dihydro-5H-[1,2,4]triazolo[3,4-i]purin-8-yl)-4-propoxybenzenesulfonamide (128)

N-(4-Hydroxy-1-methylpiperidin-4-ylmethyl)-N-methyl-3-(5-oxo-6-propyl-6,9-dihydro-5H-[1,2,4]triazolo[3,4-i]purin-8-yl)-4-propoxybenzenesulfonamide (129)

8-{2-Propoxy-5-[4-(2,2,2-trifluoroethanoyl)piperazine-1-sulfonyl]phenyl}-6-propyl-6,9-dihydro-[1,2,4]triazolo[3,4-i]purin-5-one (130)

N-(1-{[3-(5-Oxo-6-propyl-6,9-dihydro-5H-[1,2,4]triazolo[3,4-i]purin-8-yl)-4-propoxybenzenesulfonylamino]methyl}cycloheptyl)acetamide (131)

The title compounds were synthesized from the title compound of Preparation 10 following the procedure of example 115 and using the corresponding reactant, respectively. The ESI/MS data, HPLC retention times and yields are summarised in Table 3.

TABLE 3

| Example | Molecular Formula | ESI/MS m/e [M + H]+ | Retention Time (min.) | Yield % |
|---|---|---|---|---|
| 115 | $C_{25}H_{34}N_8O_5S$ | 559 | 11.7 | 82 |
| 116 | $C_{20}H_{25}N_7O_4S$ | 460 | 16.3 | 79 |
| 117 | $C_{19}H_{23}N_9O_4S$ | 445 | 16.5 | 66 |
| 118 | $C_{20}H_{25}N_7O_5S$ | 476 | 13.8 | 75 |
| 119 | $C_{20}H_{22}N_{10}O_4S$ | 499 | 15.4 | 85 |
| 120 | $C_{23}H_{32}N_8O_4S$ | 517 | 11.3 | 84 |
| 121 | $C_{24}H_{26}N_8O_4S$ | 523 | 13.1 | 72 |
| 122 | $C_{25}H_{28}N_8O_4S$ | 537 | 13.5 | 77 |
| 123 | $C_{24}H_{29}N_9O_4S$ | 540 | 11.2 | 68 |
| 124 | $C_{25}H_{34}N_8O_4S$ | 543 | 11.7 | 66 |
| 125 | $C_{25}H_{34}N_8O_4S$ | 543 | 12.0 | 79 |
| 126 | $C_{25}H_{33}N_7O_5S$ | 544 | 18.0 | 82 |
| 127 | $C_{27}H_{38}N_8O_4S$ | 571 | 11.9 | 84 |
| 128 | $C_{26}H_{36}N_8O_5S$ | 573 | 11.2 | 74 |
| 129 | $C_{26}H_{36}N_8O_5S$ | 573 | 12.6 | 87 |
| 130 | $C_{24}H_{27}F_3N_8O_5S$ | 597 | 17.3 | 65 |
| 131 | $C_{28}H_{38}N_8O_5S$ | 447 | 16.5 | 58 |

Example 132

6-Butyl-8-[5-(3-hydroxyazetidine-1-sulfonyl)-2-propoxyphenyl]-6,9-dihydro-[1,2,4]triazolo[3,4-i]purin-5-one Obtained as a white solid (50%) from the title compound of Preparation 14 and azetidin-3-ol following the procedure of example 1.

m.p. 238° C.

δ (DMSO-d6): 0.95 (3H, t), 1.02 (3H, t), 1.39 (2H, m), 1.83 (4H, m), 3.36 and 3.39 (4H, 2d), 3.90 and 3.93 (4H, 2d), 4.24 (2H, t), 4.31 (2H, t), 5.74 (1H, d), 7.51 (1H, d), 7.88 (1H, d), 8.29 (1H, s), 9.26 (1H, s), 13.8 (1H, s).

Example 133

6-Butyl-8-[5-(piperazine-1-sulfonyl)-2-propoxyphenyl]-6,9-dihydro-[1,2,4]triazolo[3,4-i]purin-5-one Obtained as a white solid (60%) from the title compound of Preparation 14 and piperazine following the procedure of example 1.

m.p. 147° C.

δ (DMSO-d6): 0.95 (3H, t), 1.02 (3H, t), 1.72 (2H, m), 1.85 (4H, m), 2.80 (2H, t), 2.85 (2H, t), 3.27 (4H, m), 4.20 (4H, m), 7.38 (1H, d), 7.79 (1H, d), 8.27 (1H, s), 9.20 (1H, s).

Example 134

3-(6-Butyl-5-oxo-6,9-dihydro-5H-[1,2,4]triazolo[3,4-i]purin-8-yl)-N-methyl-N-(1-methylazetidin-3-yl)-4-propoxybenzenesulfonamide Obtained as a white solid (19%) from the title compound of Preparation 14 and methyl(1-methylazetidin-3-yl)amine following the procedure of example 1.

m.p. 169° C.

δ (CDCl3): 1.02 (3H, t), 1.16 (3H, t), 1.48 (2H, m), 1.89 (2H, m), 2.08 (2H, m), 2.30 (3H, s), 2.75 (3H, s), 3.06 (2H, t), 3.53 (2H, t), 4.02 (1H, m), 4.39 (4H, m), 7.19 (1H, d), 7.26 (1H, s), 7.80 (1H, d), 8.74 (1H, s), 8.96 (1H, s).

Example 135

6-Butyl-8-[5-(3-dimethylaminomethylazetidine-1-sulfonyl)-2-propoxyphenyl]-6,9-dihydro-[1,2,4]triazolo[3,4-i]purin-5-one Obtained as a white solid (56%) from the title compound of Preparation 14 and the title compound of Preparation 33 following the procedure of example 1.

m.p. 198° C.

δ (DMSO-d6): 0.96 (3H, t), 1.03 (3H, t), 1.37 (2H, m), 1.80 (2H, m), 1.87 (2H, m), 1.99 (6H, s), 2.1 (2H, d), 2.51 (1H, m), 3.36 (2H, m), 3.83 (2H, t), 4.25 (2H, t), 4.31 (2H, t), 7.50 (1H, d), 7.88 (1H, d), 8.30 (1H, s), 9.24 (1H, s).

Example 136

6-Butyl-8-(5-{3-[(2-hydroxyethyl)methylamino]azetidine-1-sulfonyl}-2-propoxyphenyl)-6,9-dihydro-[1,2,4]triazolo[3,4-i]purin-5-one Obtained as a white solid (54%) from the title compound of Preparation 14 and 2-(azetidin-3-ylmethylamino)ethanol following the procedure of example 1.

m.p. 162° C.

δ (DMSO-d6): 0.46 (4H, m), 1.33 (2H, m), 1.80 (4H, m), 1.90 (3H, s), 2.18 (2H, t), 3.21 (1H, m), 3.47 (2H, t), 3.75 (2H, t), 4.24 (6H, m), 7.47 (1H, d), 7.86 (1H, d), 8.26 (1H, s), 9.23 (1H, s), 13.72 (1H, bs).

Example 137

6-Butyl-8-{5-[4-(2-hydroxy-1-methylethyl)piperazine-1-sulfonyl]-2-propoxyphenyl}-6,9-dihydro-[1,2,4]triazolo[3,4-i]purin-5-one Obtained as a white solid (65%) from the title compound of Preparation 14 and 2-piperazin-1-ylpropan-1-ol following the procedure of example 1.

m.p. 221° C.

δ (DMSO-d6): 0.86 (3H, d), 0.95 (3H, t), 1.00 (3H, t), 1.38 (2H, m), 1.83 (4H, m), 2.59 (4H, m), 2.89 (4H, m), 3.21 (1H, m), 3.39 (2H, m), 4.25 (4H, m), 7.46 (1H, d), 7.79 (1H, d), 8.21 (1H, s), 9.25 (1H, s), 13.7 (1H, s).

Example 138

6-Butyl-8-{5-[4-(2-hydroxy-1,1-dimethylethyl)piperazine-1-sulfonyl]-2-propoxyphenyl}-6,9-dihydro-[1,2,4]triazolo[3,4-i]purin-5-one Obtained as a white solid (82%) from the title compound of Preparation 14 and the title compound of Preparation 37 following the procedure of example 1.

m.p. 237° C.

δ (DMSO-d6): 0.87 (6H, s), 0.95 (3H, t), 1.02 (3H, t), 1.38 (2H, m), 1.82 (4H, m), 2.62 (4H, m), 2.86 (4H, m), 3.20 (2H, s), 4.25 (4H, m), 7.46 (1H, d), 7.77 (1H, d), 8.20 (1h, s) 9.24 (1H, s).

Examples 139–142

N,N-Bis-(2-hydroxyethyl)-3-(6-isobutyl-5-oxo-6,9-dihydro-5H-[1,2,4]triazolo[3,4-i]purin-8-yl)-4-propoxybenzenesulfonamide (139)

3-(6-Isobutyl-5-oxo-6,9-dihydro-5H-[1,2,4]triazolo[3,4-i]purin-8-yl)-N-(4-methylpiperazin-1-yl)-4-propoxybenzenesulfonamide (140)

8-{5-[4-(2-Hydroxyethyl)piperidine-1-sulfonyl]-2-propoxyphenyl}-6-isobutyl-6,9-dihydro-[1,2,4]triazolo[3,4-i]purin-5-one (141)

8-(5-{4-[2-(2-Hydroxyethoxy)ethyl]piperazine-1-sulfonyl}-2-propoxyphenyl)-6-isobutyl -6,9-dihydro-[1,2,4]triazolo[3,4-i]purin-5-one (142)

The title compounds were synthesized from the title compound of Preparation 30 following the procedure of example 115 and using the corresponding reactant respectively. The ESI/MS data, HPLC retention times and yields are summarised in Table 4.

TABLE 4

| Example | Molecular Formula | ESI/MS m/e [M + H]+ | Retention Time (min.) | Yield % |
|---|---|---|---|---|
| 139 | $C_{23}H_{31}N_7O_6S$ | 534 | 15.1 | 62 |
| 140 | $C_{24}H_{33}N_9O_4S$ | 544 | 13.1 | 78 |
| 141 | $C_{26}H_{35}N_7O_5S$ | 558 | 18.7 | 75 |
| 142 | $C_{27}H_{38}N_8O_6S$ | 603 | 13.7 | 77 |

Example 143

N-(2-Hydroxyethyl)-3-[6-(2-methoxyethyl)-5-oxo-6,9-dihydro-5H-[1,2,4]triazolo[3,4-i]purin-8-yl]-4-propoxy-N-propylbenzenesulfonamide Obtained as a white solid (43%) from the title compound of Preparation 34 and 2-propylaminoethanol following the procedure of example 1.

m.p. 183° C.

δ (DMSO-d6): 0.82 (3H, t), 0.99 (3H, t), 1.52 (2H, m), 1.87 (2H, m), 3.13 (4H, m), 3.30 (3H, s), 3.51 (2H, t), 3.79 (2H, t), 4.28 (2H, t), 4.41 (2H, t), 7.43 (1H, d), 7.89 (1H, d), 8.31 (1H, s), 9,29 (1H, s).

Example 144

3-[6-(2-Methoxyethyl)-5-oxo-6,9-dihydro-5H-[1,2,4]triazolo[3,4-i]purin-8-yl]-N-(2-morpholin-4-ylethyl)-4-propoxybenzenesulfonamide Obtained as a white solid (48%) from the title compound of Preparation 34 and 2-morpholin-4-ylethylamine following the procedure of example 1.

m.p. 171° C.

δ (DMSO-d6): 0.98 (3H, t), 1.87 (2H, n), 2.27 (6H, m), 2.89 (2H, m), 3.29 (3H, s), 3.48 (4H, m), 3.79 (2H, t), 4.27 (2H, t), 4.42 (2H, t), 7.43 (1H, d), 7.61 (1H, t), 7.87 (1H, d), 8.34 (1H, s), 9.28 (1H, s).

Example 145

8-{5-[4-(3-Hydroxypropyl)piperazine-1-sulfonyl]-2-propoxyphenyl}-6-(2-methoxyethyl)-6,9-dihydro-[1,2,4]triazolo[3,4-i]purin-5-one Obtained as a white solid (32%) from the title compound of Preparation 34 and 3-piperazin-1-ylpropan-1-ol following the procedure of example 1.

m.p. 171° C.

δ (DMSO-d6): 0.99 (3H, t), 1.50 (2H, m), 1.87 (2H, m), 2.36 (2H, m), 2.45 (4H, m), 2.92 (4H, m), 3.30 (3H, s), 3.78 (2H, t), 4.28 (2H, t), 4.41 (2H, t), 7.48 (1H, d), 7.78 (1H, d), 8.21 (1H, s), 9.28 (1H, s).

Example 146

3-[6-(2-Methoxyethyl)-5-oxo-6,9-dihydro-5H-[1,2,4]triazolo[3,4-i]purin-8-yl]-N-(3-morpholin-4-ylpropyl)-4-propoxybenzenesulfonamide Obtained as a white solid (47%) from the title compound of Preparation 34 and 3-morpholin-4-ylpropylamine following the procedure of example 1.

m.p. 149° C.

δ (DMSO-d6): 0.96 (3H, t), 1.49 (2H, m), 1.84 (2H, m), 2.19 (6H, m), 2.78 (2H, m), 3.27 (3H, s), 3.45 (4H, m), 3.76 (2H, t), 4.25 (2H, t), 4.39 (2H, t), 7.41 (1H, d), 7.62 (1H, t), 7.81 (1H, d), 8.31 (1H, s), 9.25 (1H, s).

Examples 147–149

N,N-Bis-(2-hydroxyethyl)-3-(5-oxo-6-pentyl-6,9-dihydro-5H-[1,2,4]triazolo[3,4-i]purin-8-yl)-4-propoxybenzenesulfonamide (147)

8-{5-[4-(2-Hydroxyethyl)piperidine-1-sulfonyl]-2-propoxyphenyl}-6-pentyl-6,9-dihydro-[1,2,4]triazolo[3,4-i]purin-5-one (148)

8-(5-{4-[2-(2-Hydroxyethoxy)ethyl]piperazine-1-sulfonyl}-2-propoxyphenyl)-6-pentyl-6,9-dihydro-[1,2,4]triazolo[3,4-i]purin-5-one (149)

The title compounds were synthesized from the title compound of Preparation 32 following the procedure of example 115 and using the corresponding reactant respectively. The ESI/MS data, HPLC retention times and yields are summarised in Table 5.

TABLE 5

| Example | Molecular Formula | ESI/MS m/e [M + H]⁺ | Retention Time (min.) | Yield % |
|---|---|---|---|---|
| 147 | $C_{24}H_{33}N_7O_6S$ | 548 | 16.7 | 85 |
| 148 | $C_{27}H_{37}N_7O_5S$ | 572 | 20.3 | 65 |
| 149 | $C_{28}H_{40}N_8O_6S$ | 617 | 15.0 | 72 |

The following examples illustrate pharmaceutical compositions according to the present invention and procedure for their preparation.

Composition Example 1

50,000 capsules each containing 100 mg of active ingredient were prepared according to the following formulation:

| Active ingredient | 5 Kg |
|---|---|
| Lactose monohydrate | 10 Kg |
| Colloidal silicone dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 Tablets each containing 50 mg of active ingredient were prepared from the following formulation:

| Active ingredient | 2.5 Kg |
|---|---|
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:
1. A compound of formula (I):

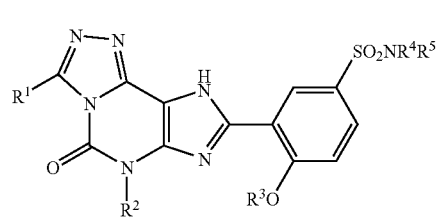

wherein:
$R^1$ represents hydrogen, a $C_1$–$C_4$ alkyl group or a group of formula

—(CH₂)ₙR⁶ wherein n is 0, 1 or 2 and $R^6$ represents phenyl, pyridyl or morpholinyl;

$R^2$ and $R^3$ independently represent a $C_1$–$C_5$ alkyl group, a $C_{3-10}$ cycloalkyl group, or a group of formula

—(CH₂)ₙR⁶ wherein n is 0, 1 or 2 and $R^6$ represents an unsubstituted or substituted phenyl or pyridyl group;

either $R^4$ and $R^5$ together with the nitrogen atom to which they are attached form a 3 to 7-membered ring comprising a total of from 1 to 4 heteroatoms selected from nitrogen, oxygen and sulphur, which ring may be unsubstituted or substituted by one or more halogen atoms or hydroxy, oxoalkyl, carbamoyl, hydroxycarbonyl, alkoxycarbonyl, trifluoroacetyl, amino, monoor di-alkylamino groups or an alkylene group, or one or more alkyl, alkenyl or alkynyl groups which may in turn be unsubstituted or substituted by one or more halogen atoms or hydroxy, alkoxy, hydroxyalkoxy, amino or mono- or di-alkylamino groups, or $R^4$ and $R^5$ independently represent hydrogen, an amidino group or an alkyl, alkenyl or alkynyl group which may be unsubstituted or substituted by one or more halogen atoms or hydroxy, alkoxy, alkylthio, amino, mono- or di-alkylamino groups, or $R^4$ represents hydrogen or an alkyl group and $R^5$ represents a group of formula —(CH$_2$)$_n$—R$^7$ wherein n is an integer from 0 to 4 and $R^7$ represents: a cycloalkyl group which may be unsubstituted or substituted by one or more halogen atoms or alkyl, hydroxy, alkylenedioxy, alkoxy, amino, mono- or di-alkylamino, alkylamido, nitro, cyano or trifluoromethyl groups; a phenyl group which may be unsubstituted or substituted by one or more halogen atoms or alkyl, hydroxy, alkylenedioxy, alkoxy, amino, mono- or di-alkylamino, nitro, cyano or trifluoromethyl groups; or a 3 to 7-membered ring comprising from 1 to 4 heteroatoms selected from nitrogen, oxygen and sulphur, which ring may be unsubstituted or substituted by one or more halogen atoms or hydroxy, alkoxy, phenyl, alkoxycarbonyl, amino, mono-alkylamino, di-alkylamino or hydroxycarbonyl groups or one or more alkyl groups which may be unsubstituted or substituted by one or more halogen atoms or hydroxy, alkoxy, hydroxyalkoxy, phenyl, alkoxycarbonyl, amino, mono- or di-alkylamino or hydroxycarbonyl groups;

or a pharmaceutically acceptable salt thereof.

2. A compound according to claim 1 wherein $R^1$ represents hydrogen, a $C_1$–$C_4$ alkyl group or a group of formula —(CH$_2$)$_n$R$^6$ wherein n is 0, 1 or 2 and $R^6$ represents phenyl, pyridyl or morpholinyl.

3. A compound according to claim 1 wherein $R^2$ and $R^3$ independently represent a $C_1$–$C_5$ alkyl group, a $C_{3-10}$ cycloalkyl group, or a group of formula —(CH$_2$)$_n$R$^6$ wherein n is 0, 1 or 2 and $R^6$ represents an unsubstituted or substituted phenyl or pyridyl group.

4. A compound according to claim 1 wherein $R^1$ is hydrogen or a methyl, ethyl, propyl, pyridyl, pyridylmethyl, benzyl or N-morpholinylmethyl group; $R^2$ is an ethyl, propyl, n-butyl, i-butyl, n-pentyl, methoxyethyl, substituted or unsubstituted benzyl or 3-pyridylmethyl group; and $R^3$ is an ethyl, propyl or n-butyl group.

5. A compound according to claim 1 wherein the ring formed by $R^4$, $R^5$ and the nitrogen atom to which they are attached is a piperidyl, piperazinyl, [1,4]diazepan-1-yl, morpholinyl, pyrazolyl or azetidinyl group which is unsubstituted or substituted by one or more groups selected from a $C_1$–$C_4$ alkyl, $C_2$–$C_4$ alkenyl, carbamoyl, amino, di-$C_1$–$C_4$-alkylamino, (2-hydroxyethyl)methylamino, hydroxyl, 2,2,2-trifluoroethanoyl, 2,2,2-trifluoroethyl, formyl and hydroxyalkyl groups, alkoxyalkyl groups and hydroxyalkoxyalkyl groups wherein the alkyl moieties contain from 1 to 4 carbon atoms.

6. A compound according to claim 5 wherein $R^4$ and $R^5$ together with the nitrogen atom to which they are attached represent a 4-hydroxypiperidyl, 4-carbamoylpiperidyl, 3-carbamoylpiperidyl, piperazinyl, 4-methylpiperazinyl, 4-ethylpiperazinyl, 4-formylpiperazinyl, [1,4]-diazepan-1-yl, 4-methyl-[1,4]-diazepan-1-yl, 4-(2-hydroxyethyl)piperazinyl, 4-[2-(2-hydroxyethoxy)ethyl]piperazinyl, morpholinyl, aminopyrazolyl, diazabicyclo[2.2.1]hept-2-yl, 5-methyldiazabicyclo[2.2.1]hept-2-yl, 5-(2-hydroxyethyl)-diazabicyclo[2.2.1]hept-2-yl, 3(S)-methylpiperazinyl, 3(R)-methylpiperazinyl, (3R,5S)-3,5-dimethylpiperazinyl, (2R,5S)-2,5-dimethylpiperazinyl, (2S,5R)-2,5-dimethyl piperazinyl, 3-dimethylaminoazetidinyl, 3-dimethylaminomethylazetidinyl, 4-allylpiperazinyl, 4-propylpiperazinyl, (3R,5S)-3,4,5-trimethylpiperazinyl, 4-(2-methoxyethyl)-piperazinyl, 4-(2-hydroxyethyl)[1,4]diazepan-1-yl, 4-(2-hydroxy-1-methylethyl)piperazinyl, 4-(2-hydroxy -1,1-dimethylethyl)piperazinyl, 4-(2,2,2-trifluoroethyl)-piperazinyl, 4-(3-hydroxypropyl)piperazinyl, 4-(isopropyl) piperazinyl, 4-(2-ethoxyethyl)piperazinyl, 4-(2,2,2-trifluoroethanoyl) piperazinyl, 3-hydroxyazetidinyl, 3-(2-hydroxyethyl)methylaminoazetidinyl or 4-(2-hydroxyethyl)-piperidyl group.

7. A compound according to claim 1 wherein $R^4$ and $R^5$ independently represent hydrogen, a $C_1$–$C_4$ alkyl group which is unsubstituted or substituted by a hydroxy or dimethyl amino group, a propynyl group or an amidino group.

8. A compound according to claim 1 wherein $R^4$ is hydrogen or a $C_1$–$C_4$ alkyl group and $R^5$ represents a group of formula —(CH$_2$)$_n$R$^7$ wherein n is 0, 1, 2 or 3 and $R^7$ is a pyridyl, piperidyl, piperazinyl, morpholinyl, triazolyl, tetrazolyl, pyrrolidinyl, 1-ethylaminocyclohex-1-yl, 1-diethylaminocyclohex-1-yl, 1-ethylaminocyclohept-1-yl, 1-diethylaminocyclohept-1-yl, 3,4-dimethoxyphenyl, 1-methyl-4-phenylpiperidin-4-yl, imidazoyl, 1-methylpiperid-4-yl, tetrahydrofuranyl, 2,2,6,6,-tetramethylpiperid-4-yl, 4-hydroxypiperid-4-yl, 1-acetamidocyclohept-1-yl, 1-methyl-3-azetidinyl or 4-methylpiperazin-1-yl group.

9. A compound according to claim 1 which is 6-ethyl-8-[5-(4-methylpiperazine-1-sulphonyl)-2-propoxyphenyl]-6,9-dihydro-[1,2,4]triazolo[3,4-i]purin-5-one, 8-[2-butoxy-5-(4-methylpiperazine-1-sulfonyl)phenyl]-6-ethyl-6,9-dihydro-[1,2,4]triazolo[3,4-i]purin-5-one, 8-[5-(4-methylpiperazine-1-sulfonyl)-2-propoxyphenyl]-6-propyl-6,9-dihydro-[1,2,4]triazolo[3,4-i]purin-5-one, 8-{5-[4-(2-hydroxyethyl)piperazine-1-sulphonyl]-2-propoxyphenyl}-6-propyl-6,9-dihydro-[1,2,4]triazolo[3,4-i]purin-5-one, 8-[5-(4-methyl-[1,4]diazepane-1-sulfonyl)-2-propoxyphenyl]-6-propyl-6,9-dihydro-[1,2,4]triazolo[3,4-i]purin-5-one, 6-butyl-8-{5-[4-(2-hydroxyethyl)piperazine-1-sulfonyl]-2-propoxyphenyl}-6,9-dihydro-[1,2,4]triazolo[3,4-i]purin-5-one, 3-(5-oxo-6-propyl-6,9-dihydro-5H-[1,2,4]triazolo[3,4-i]purin-8-yl)-4-propoxy-N-pyridin-4-ylbenzenesulphonamide;

8-[5-((S)-3-Methylpiperazine-1-sulfonyl)-2-propoxyphenyl]-6-propyl-6,9-dihydro-[1,2,4]triazolo[3,4-i]purin-5-one, 8-[5-((1S,4S)-5-Methyl-2,5-diazabicyclo[2.2.1]heptane-2-sulfonyl)-2-propoxyphenyl]-6-propyl-6,9-dihydro-[1,2,4]triazolo[3,4-i]purin-5-one, 8-[5-(3-Dimethylaminomethylazetidine-1-sulfonyl)-2-propoxyphenyl]-6-propyl-6,9-dihydro-[1,2,4]triazolo[3,4-i]purin-5-one, 8-[5-((3R,5S)-3,5-Dimethylpiperazine-1-sulfonyl)-2-propoxyphenyl]-6-propyl-6,9-dihydro-[1,2,4]triazolo[3,4-i]purin-5-one, N-(3-Dimethylamino-2,2-dimethylpropyl)-3-(oxopropyl-6,9-dihydro-5H-[1,2,4]triazolo[3,4-i]purin-8-yl)-4-propoxy benzenesulfonamide, 8-{5-[4-(2-Hydroxyethyl)-[1,4]diazepane-1-sulfonyl]-2-propoxyphenyl}-6-propyl-6,9-dihydro-[1,2,4]triazolo[3,4-i]purin-5-one, 8-{5-[4-(2-Hydroxy-1,1-dimethylethyl)piperazine-1-sulfonyl]-2-propoxyphenyl}-6-propyl-6,9-dihydro-[1,2,4]triazolo[3,4i]purin-5-one, 6-Butyl-8-{5-[4-(2-hydroxy-1,1-dimethylethyl)piperazine-1-sulfonyl]-2-propoxyphenyl}-6,9-dihydro-[1,2,4]triazolo[3,4-i]purin-5-one or a pharmaceutically acceptable salt thereof.

10. A process for preparing a compound as defined in claim 1 which process comprises reacting a hydrazinopurine derivative of formula (II)

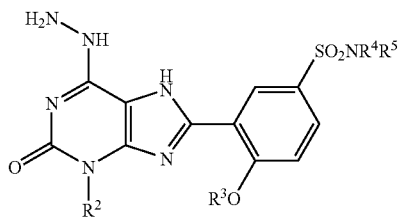

(II)

wherein $R^2$, $R^3$, $R^4$ and $R^5$ are as defined in claim 1, with a carboxylic acid of the general formula (III):

$R^1$—$CO_2H$ (III)

wherein $R^1$ is as defined in claim 1, or a reactive derivative thereof optionally in the presence of a polar aprotic solvent.

11. A process according to claim 10 wherein said reaction is carried out in the presence of an organic base.

12. A process for preparing a compound as defined in claim 1 which process comprises reacting a phenylxanthine of formula (IX):

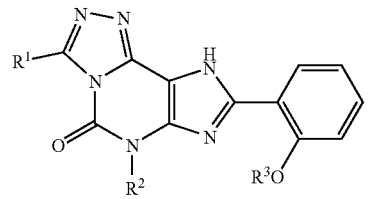

(IX)

wherein $R^1$, $R^2$ and $R^3$ are as defined in claim 1, with chlorosulphonic acid so as to obtain the sulphonyl chloride of formula (X):

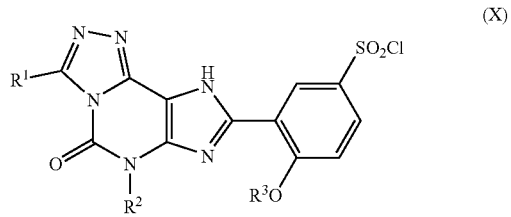

(X)

wherein $R^1$, $R^2$ and $R^3$ are as defined in claim 1, and reacting the sulphonyl chloride of formula (X) with an amine of formula (VIII):

(VIII)

wherein $R^4$ and $R^5$ are as defined in claim 1.

13. A process according to claim 12 wherein the reaction forming the sulphonyl chloride of formula (X) is carried using an excess of the chlorosulphonic acid or using the chlorosulphonic acid as a solvent, and the conversion of the sulphonyl chloride of formula (X) is carried out in a polar aprotic solvent and in the presence of an organic base.

14. A pharmaceutical composition comprising as an active ingredient, at least one compound as defined in claim 1 or a pharmaceutically acceptable salt thereof, and a pharmaceutically acceptable excipient.

15. A method of treating a human or animal patient suffering from stable, unstable or variant angina, hypertension, pulmonary hypertension, congestive heart failure, atherosclerosis, conditions of reduced blood vessel patency, bronchitis, chronic asthma, allergic asthma, allergic rhinitis, glaucoma, male erectile dysfunction or female sexual dysfunction which method comprises administering to said patient requiring such treatment an effective amount of a compound as defined in claim 1.

* * * * *